US011589864B2

(12) United States Patent
Vyas et al.

(10) Patent No.: US 11,589,864 B2
(45) Date of Patent: Feb. 28, 2023

(54) STAPLER APPARATUS AND METHODS FOR USE

(71) Applicants: Dinesh Vyas, Elk Grove, CA (US); Anoushka Vyas, Elk Grove, CA (US)

(72) Inventors: Dinesh Vyas, Elk Grove, CA (US); Anoushka Vyas, Elk Grove, CA (US)

(73) Assignee: Dinesh Vyas, Elk Grove, CA (US)

( * ) Notice: Subject to any disclaimer, the term of this patent is extended or adjusted under 35 U.S.C. 154(b) by 2 days.

(21) Appl. No.: 16/874,630

(22) Filed: May 14, 2020

(65) Prior Publication Data

US 2021/0177404 A1 Jun. 17, 2021

Related U.S. Application Data

(60) Provisional application No. 62/947,903, filed on Dec. 13, 2019.

(51) Int. Cl.
*A61B 17/068* (2006.01)
*A61B 8/08* (2006.01)
(Continued)

(52) U.S. Cl.
CPC ........ *A61B 17/0686* (2013.01); *A61B 1/3132* (2013.01); *A61B 5/026* (2013.01);
(Continued)

(58) Field of Classification Search
CPC ... A61B 17/0686; A61B 1/3132; A61B 5/026; A61B 8/488; A61B 2017/00084;
(Continued)

(56) References Cited

U.S. PATENT DOCUMENTS 3,612,107 A * 10/1971 Grise ..................... F16K 7/06
24/135 R
3,940,844 A * 3/1976 Colby .................... B21D 53/46
29/450
(Continued)

FOREIGN PATENT DOCUMENTS

EP 1157666 A1 11/2001
WO 2013134411 A1 9/2013

OTHER PUBLICATIONS

Park, Hye Lyun, Authorized officer for Korean Intellectual Property Office, International Search Report and Written Opinion for corresponding International Application No. PCT/US2020/064732, dated Jun. 9, 2021, 16 pages.

*Primary Examiner* — Robert F Long
(74) *Attorney, Agent, or Firm* — William A. English; Vista IP Law Group LLP

(57) ABSTRACT

Apparatus and methods are provided for performing a medical procedure, such as a laparoscopic appendectomy using a stapler apparatus including a reusable handle portion including a shaft include proximal and distal ends, a disposable end effector attached to the distal end of the shaft of the reusable handle carrying one or more staples. For example, the end effector may include first and second jaws movable relative to one another between open and closed positions, the first jaw carrying a cartridge which includes the one or more staples. A Doppler sensor, a cutting element, and, optionally, a thermal element are also provided on the end effector. The end effector is introduced into a patient's body, tissue is positioned/locked between the jaws, and a plurality of staples are deployed into the tissue. The Doppler sensor is used to confirm that blood flow has discontinued in the stapled tissue, and the cutting element is actuated to sever the stapled tissue.

17 Claims, 35 Drawing Sheets

(51) Int. Cl.
*A61B 5/026* (2006.01)
*A61B 1/313* (2006.01)
*A61B 17/072* (2006.01)
*A61B 17/00* (2006.01)

(52) U.S. Cl.
CPC ...... *A61B 8/488* (2013.01); *A61B 2017/0023* (2013.01); *A61B 2017/0046* (2013.01); *A61B 2017/00084* (2013.01); *A61B 2017/00823* (2013.01); *A61B 2017/07257* (2013.01); *A61B 2017/07271* (2013.01); *A61B 2017/07285* (2013.01)

(58) Field of Classification Search
CPC .. A61B 2017/0046; A61B 2017/07257; A61B 2017/0023; A61B 2017/07285; A61B 2017/00823; A61B 2017/07271; A61B 90/361; A61B 2090/309; A61B 18/085; A61B 2018/00482; A61B 2018/00607; A61B 2018/00601; A61B 2018/00595; A61B 2018/1455; A61B 18/1445; A61B 2017/00022; A61B 17/0644; A61B 2017/07235; A61B 17/07207; A61B 2017/07228; A61B 2090/372; A61B 2017/00115; A61B 90/37; A61B 2017/00473; A61B 1/018; A61B 1/00135; A61B 1/00087; A61B 1/00181; A61B 1/00052; A61B 5/6847; A61B 5/0265
USPC ............................................. 227/175.1–182.1
See application file for complete search history.

(56) References Cited

U.S. PATENT DOCUMENTS

| | | | | | |
|---|---|---|---|---|---|
| 4,423,787 | A | * | 1/1984 | Steinberg | A01B 35/24 172/142 |
| 4,487,394 | A | * | 12/1984 | Rothfuss | A61B 17/076 254/28 |
| 4,526,174 | A | * | 7/1985 | Froehlich | A61B 17/0684 206/438 |
| 4,655,222 | A | * | 4/1987 | Florez | A61B 17/0644 606/219 |
| 4,676,245 | A | * | 6/1987 | Fukuda | A61B 17/08 606/216 |
| 4,706,864 | A | * | 11/1987 | Jacobsen | B25C 1/001 227/109 |
| 4,787,387 | A | * | 11/1988 | Burbank, III | A61B 17/0644 227/176.1 |
| 4,802,478 | A | * | 2/1989 | Powell | A61B 17/0684 606/138 |
| 4,848,637 | A | | 7/1989 | Pruitt | |
| 4,887,601 | A | * | 12/1989 | Richards | A61B 17/0644 606/219 |
| 4,919,021 | A | * | 4/1990 | Franks | B25B 7/02 29/243.56 |
| 4,924,864 | A | * | 5/1990 | Danzig | A61B 17/122 606/142 |
| 5,095,590 | A | * | 3/1992 | Schick | F16G 3/04 24/33 B |
| 5,163,598 | A | * | 11/1992 | Peters | A61B 17/0686 227/124 |
| 5,192,288 | A | * | 3/1993 | Thompson | A61B 17/128 227/901 |
| 5,250,058 | A | * | 10/1993 | Miller | A61B 17/11 24/615 |
| 5,258,016 | A | * | 11/1993 | DiPoto | A61B 17/0401 606/104 |
| 5,282,829 | A | * | 2/1994 | Hermes | A61B 17/064 411/479 |
| 5,389,098 | A | * | 2/1995 | Tsuruta | A61B 17/00234 606/41 |
| 5,423,857 | A | * | 6/1995 | Rosenman | A61B 17/064 411/457 |
| 5,489,058 | A | * | 2/1996 | Plyley | A61B 17/064 227/176.1 |
| 5,497,933 | A | * | 3/1996 | DeFonzo | A61B 17/0684 227/175.1 |
| 5,573,543 | A | * | 11/1996 | Akopov | A61B 17/04 227/175.1 |
| 5,643,291 | A | * | 7/1997 | Pier | A61B 17/1285 606/143 |
| 5,658,312 | A | * | 8/1997 | Green | A61B 17/064 606/213 |
| 5,709,680 | A | | 1/1998 | Yates et al. | |
| 5,893,855 | A | * | 4/1999 | Jacobs | A61B 17/0684 606/150 |
| 5,984,692 | A | * | 11/1999 | Kumagai | H05K 3/368 439/66 |
| 6,003,517 | A | | 12/1999 | Sheffield et al. | |
| 6,059,787 | A | * | 5/2000 | Allen | A61B 17/0642 606/75 |
| 6,254,615 | B1 | * | 7/2001 | Bolduc | A61B 17/12136 606/151 |
| 6,419,682 | B1 | * | 7/2002 | Appleby | A61B 17/1222 206/339 |
| 6,530,933 | B1 | * | 3/2003 | Yeung | A61B 17/0401 128/898 |
| 6,739,374 | B1 | * | 5/2004 | Mouzakis | E06B 9/36 160/349.2 |
| 6,981,983 | B1 | * | 1/2006 | Rosenblatt | A61B 17/0401 128/898 |
| 7,048,255 | B2 | * | 5/2006 | Buch | B25C 11/00 254/25 |
| 7,267,682 | B1 | * | 9/2007 | Bender | A61B 17/0644 606/151 |
| 7,438,209 | B1 | * | 10/2008 | Hess | A61B 17/0644 227/180.1 |
| 7,699,860 | B2 | * | 4/2010 | Huitema | A61B 17/083 606/158 |
| 7,780,663 | B2 | | 8/2010 | Yates et al. | |
| 7,871,416 | B2 | * | 1/2011 | Phillips | A61B 17/122 606/151 |
| 7,875,063 | B1 | * | 1/2011 | Sander | A61B 17/068 606/300 |
| 7,918,873 | B2 | * | 4/2011 | Cummins | A61B 17/0644 606/219 |
| 8,123,795 | B1 | * | 2/2012 | Knodel | A61F 2/07 623/1.23 |
| 8,216,236 | B2 | | 7/2012 | Heinrich et al. | |
| 8,303,585 | B2 | | 11/2012 | Mollenauer | |
| 8,348,131 | B2 | * | 1/2013 | Omaits | A61B 17/0644 227/181.1 |
| 8,523,043 | B2 | | 9/2013 | Ullrich et al. | |
| 8,662,369 | B1 | * | 3/2014 | Manoux | A61B 90/03 227/175.1 |
| 8,763,878 | B2 | * | 7/2014 | Euteneuer | A61F 2/0063 227/179.1 |
| 9,254,131 | B2 | * | 2/2016 | Soltz | A61B 17/068 |
| 9,414,841 | B2 | * | 8/2016 | Euteneuer | A61B 17/84 |
| 9,655,618 | B2 | | 5/2017 | Knodel et al. | |
| 9,724,096 | B2 | * | 8/2017 | Thompson | A61B 17/07207 |
| 9,750,502 | B2 | * | 9/2017 | Scirica | A61B 17/0644 |
| 9,775,623 | B2 | * | 10/2017 | Zammataro | A61B 17/1285 |
| 9,848,874 | B2 | * | 12/2017 | Kostrzewski | A61B 17/0644 |
| 9,872,683 | B2 | | 1/2018 | Hopkins et al. | |
| 10,098,642 | B2 | * | 10/2018 | Baxter, III | A61B 17/32 |
| 10,188,275 | B2 | | 1/2019 | Sonnenschein et al. | |
| 10,245,038 | B2 | | 4/2019 | Hopkins et al. | |
| 10,426,467 | B2 | | 10/2019 | Miller et al. | |
| 10,426,481 | B2 | * | 10/2019 | Aronhalt | A61B 17/105 |
| 10,542,979 | B2 | * | 1/2020 | Shelton, IV | A61B 17/068 |
| 10,595,887 | B2 | | 3/2020 | Shelton, IV et al. | |
| 10,595,930 | B2 | | 3/2020 | Scheib et al. | |
| 10,624,616 | B2 | | 4/2020 | Mukherjee et al. | |
| 10,980,539 | B2 | * | 4/2021 | Harris | A61B 17/07292 |
| 11,020,111 | B2 | * | 6/2021 | Euteneuer | A61B 17/0642 |
| 11,090,045 | B2 | | 8/2021 | Shelton, IV | |

(56) References Cited

U.S. PATENT DOCUMENTS

| | | | | |
|---|---|---|---|---|
| 2001/0044656 | A1* | 11/2001 | Williamson, IV | A61B 17/0469 623/2.11 |
| 2002/0173786 | A1 | 11/2002 | Kortenbach et al. | |
| 2004/0006372 | A1* | 1/2004 | Racenet | A61B 17/072 606/219 |
| 2005/0288707 | A1* | 12/2005 | De Canniere | A61B 17/10 606/219 |
| 2006/0180633 | A1 | 8/2006 | Emmons | |
| 2006/0235469 | A1* | 10/2006 | Viola | A61B 17/0643 606/219 |
| 2007/0244351 | A1* | 10/2007 | Wazer | A61N 5/1027 600/3 |
| 2008/0065153 | A1* | 3/2008 | Allard | A61B 17/0644 606/219 |
| 2008/0082124 | A1* | 4/2008 | Hess | A61B 17/064 606/219 |
| 2009/0062799 | A1* | 3/2009 | Holsten | A61B 17/0644 606/75 |
| 2009/0065552 | A1* | 3/2009 | Knodel | A61B 17/115 227/180.1 |
| 2009/0105815 | A1* | 4/2009 | Krever | A61F 2/2466 623/2.36 |
| 2009/0134194 | A1* | 5/2009 | Maksimoski | B25C 5/02 227/120 |
| 2009/0255976 | A1* | 10/2009 | Marczyk | A61B 17/072 227/178.1 |
| 2009/0255978 | A1* | 10/2009 | Viola | A61B 17/105 227/180.1 |
| 2009/0272783 | A1* | 11/2009 | Crainich | A61B 17/0401 227/176.1 |
| 2009/0277946 | A1* | 11/2009 | Marczyk | A61B 17/07207 227/176.1 |
| 2009/0277948 | A1* | 11/2009 | Beardsley | A61B 17/068 227/178.1 |
| 2009/0281554 | A1* | 11/2009 | Viola | A61B 17/07207 606/142 |
| 2010/0100138 | A1* | 4/2010 | Reynolds | A61B 17/7059 606/86 A |
| 2010/0114124 | A1* | 5/2010 | Kelleher | A61B 17/1227 606/151 |
| 2010/0191258 | A1* | 7/2010 | Harris | A61B 17/0644 606/144 |
| 2010/0191262 | A1* | 7/2010 | Harris | A61B 17/0644 606/151 |
| 2010/0237128 | A1* | 9/2010 | Miller | A61B 17/0642 227/175.1 |
| 2010/0249496 | A1 | 9/2010 | Cardenas et al. | |
| 2010/0249499 | A1 | 9/2010 | Whitman | |
| 2010/0264192 | A1* | 10/2010 | Marczyk | A61B 17/07207 227/176.1 |
| 2010/0327042 | A1* | 12/2010 | Amid | A61B 17/0684 227/176.1 |
| 2011/0006104 | A1* | 1/2011 | Felix | A61B 17/128 227/179.1 |
| 2011/0046666 | A1* | 2/2011 | Sorrentino | A61B 17/064 606/219 |
| 2011/0063428 | A1 | 3/2011 | Sonnenschein et al. | |
| 2011/0101069 | A1* | 5/2011 | Bombard | A61B 17/1152 227/176.1 |
| 2011/0245578 | A1* | 10/2011 | Wazer | A61N 5/1027 600/3 |
| 2012/0059394 | A1 | 3/2012 | Brenner et al. | |
| 2012/0193398 | A1* | 8/2012 | Williams | A61B 17/105 227/179.1 |
| 2012/0193399 | A1* | 8/2012 | Holcomb | A61B 17/0644 227/181.1 |
| 2012/0209318 | A1* | 8/2012 | Qadeer | A61B 17/0644 606/213 |
| 2013/0030438 | A1* | 1/2013 | Fox | A61B 17/0682 606/75 |
| 2013/0153628 | A1* | 6/2013 | Euteneuer | A61B 17/17 227/175.1 |
| 2013/0233908 | A1* | 9/2013 | Knodel | A61B 17/068 227/177.1 |
| 2013/0240595 | A1* | 9/2013 | Penna | A61B 17/07207 227/175.1 |
| 2014/0144968 | A1* | 5/2014 | Shelton, IV | A61B 17/07292 227/175.1 |
| 2014/0213848 | A1 | 7/2014 | Moskowitz et al. | |
| 2014/0263570 | A1* | 9/2014 | Hopkins | A61B 17/07207 227/180.1 |
| 2014/0318687 | A1* | 10/2014 | Boettcher | B32B 7/12 156/92 |
| 2015/0238187 | A1* | 8/2015 | Schellin | B29C 67/20 227/180.1 |
| 2015/0297227 | A1* | 10/2015 | Huitema | A61B 90/03 227/177.1 |
| 2015/0351758 | A1* | 12/2015 | Shelton, IV | A61B 17/0644 606/219 |
| 2016/0051259 | A1* | 2/2016 | Hopkins | A61B 17/07207 227/176.1 |
| 2016/0135806 | A1* | 5/2016 | Euteneuer | A61B 17/068 227/175.1 |
| 2016/0317157 | A1* | 11/2016 | Bachar | A61B 17/1227 |
| 2016/0345973 | A1* | 12/2016 | Marczyk | A61B 17/07207 |
| 2016/0345974 | A1* | 12/2016 | Marczyk | A61B 17/0644 |
| 2016/0367300 | A1* | 12/2016 | Caldarella | A61B 17/808 |
| 2016/0374685 | A1* | 12/2016 | Abbott | A61B 17/07207 606/157 |
| 2017/0065276 | A1* | 3/2017 | Weiner | A61B 17/0642 |
| 2017/0354408 | A1* | 12/2017 | Kostrzewski | A61N 5/1007 |
| 2018/0028181 | A1* | 2/2018 | Alzaga | A61B 17/0684 |
| 2018/0256161 | A1 | 9/2018 | Eschbach | |
| 2019/0059894 | A1 | 2/2019 | Kumada et al. | |
| 2019/0321042 | A1* | 10/2019 | Marczyk | A61B 17/07207 |
| 2020/0214703 | A1 | 7/2020 | Thompson et al. | |
| 2021/0186511 | A1 | 6/2021 | Shellenberger | A61B 17/122 |
| 2022/0008068 | A1* | 1/2022 | Vyas | A61B 1/042 |

* cited by examiner

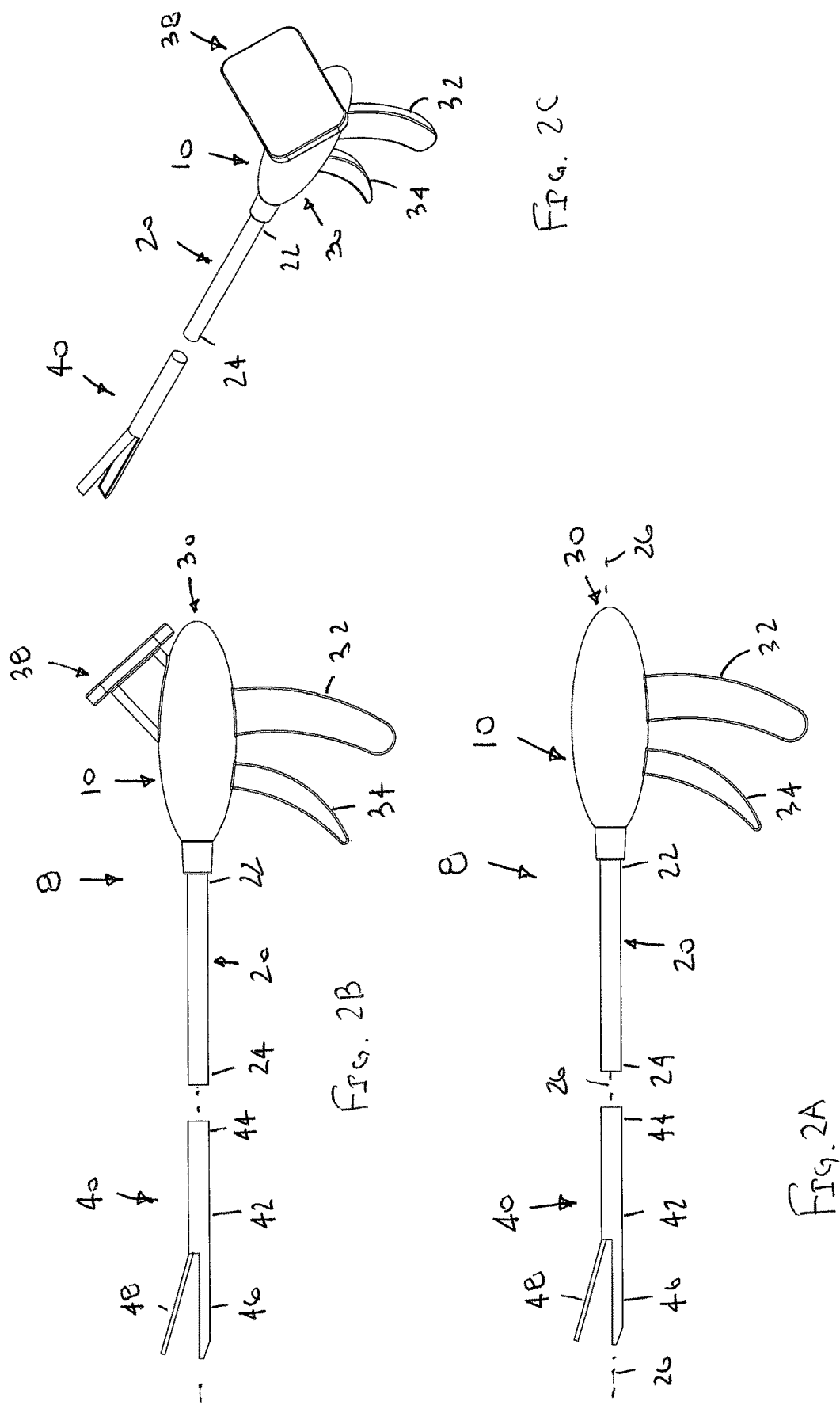

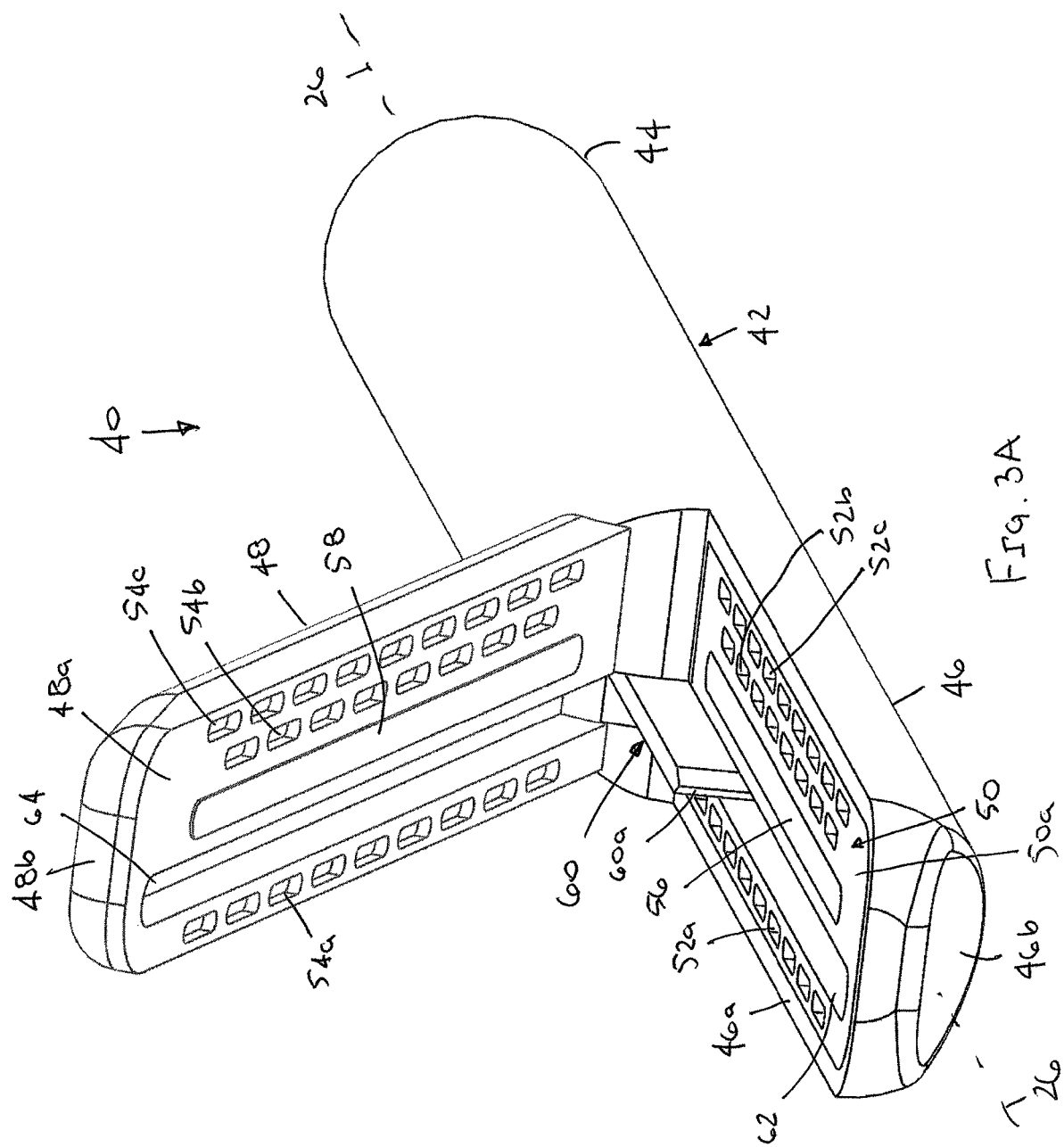

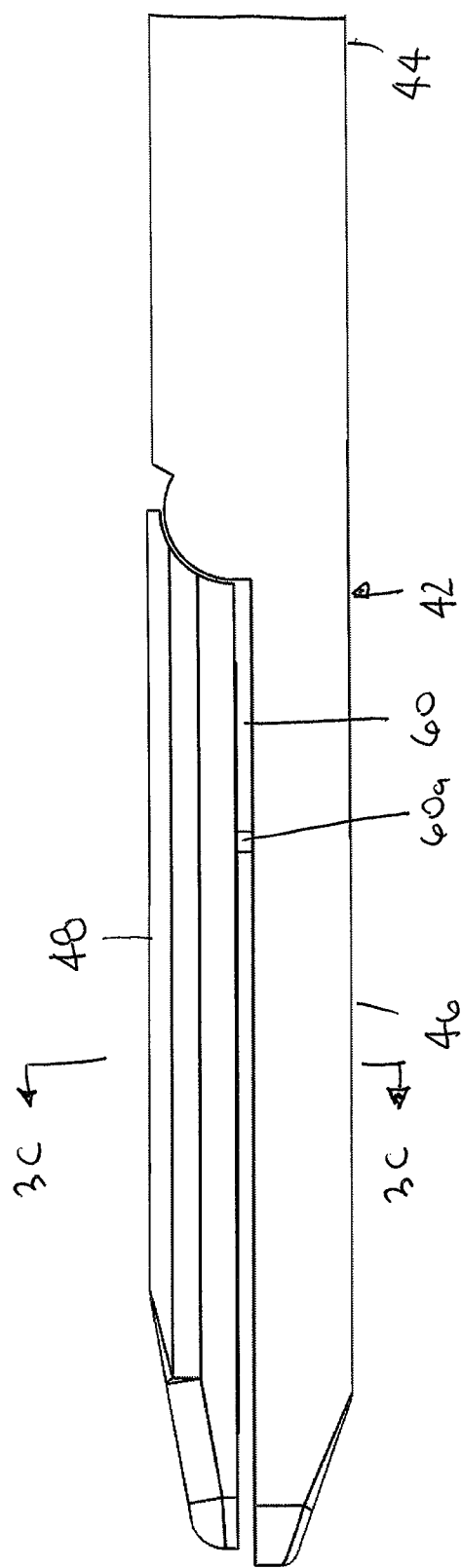

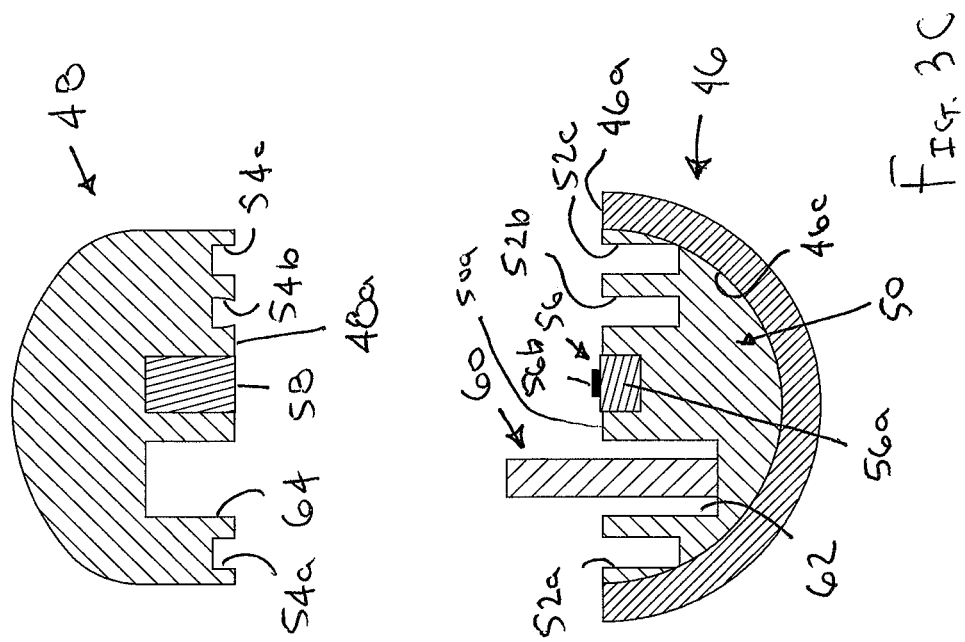

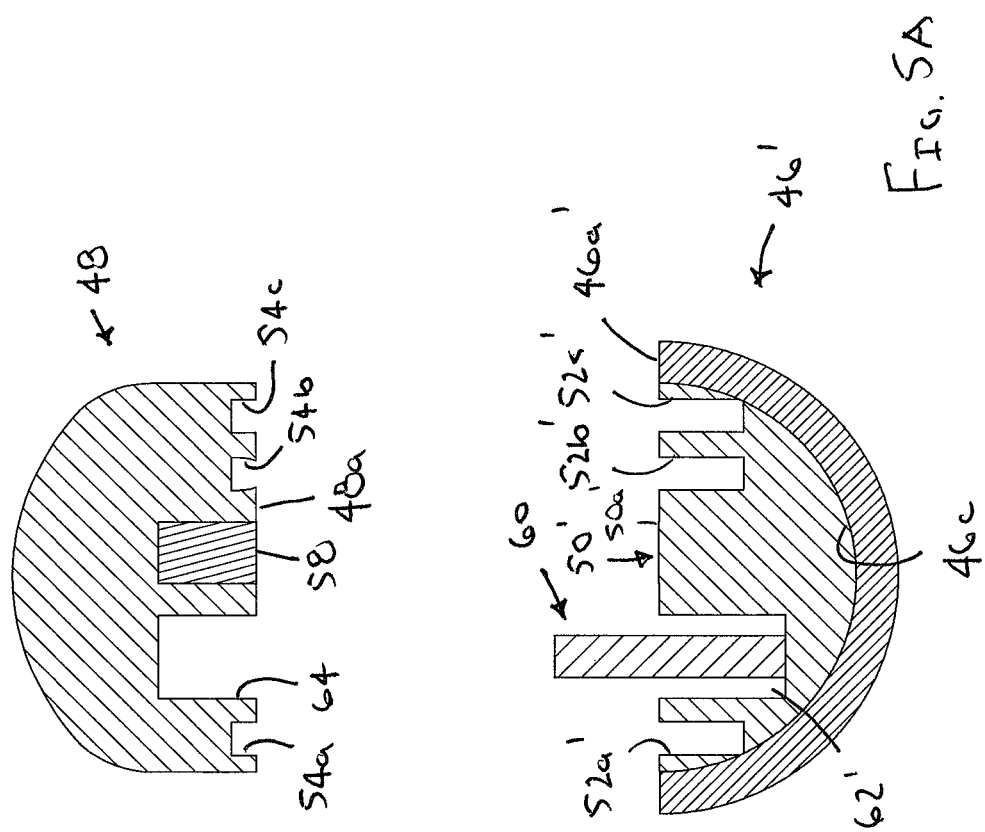

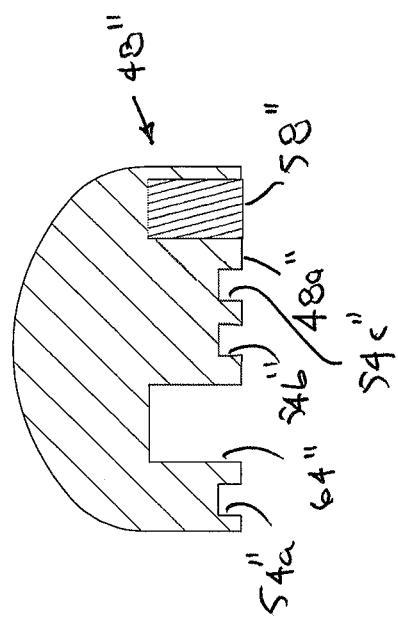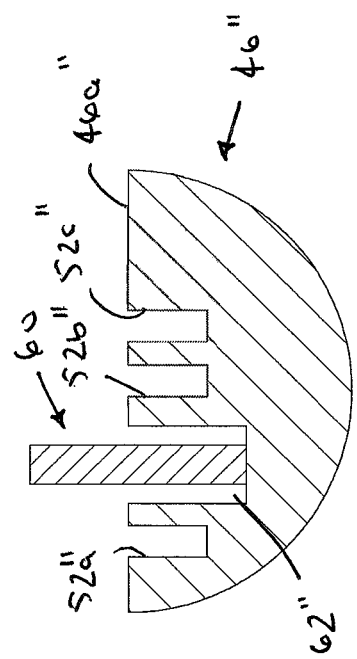
Fig. 5B

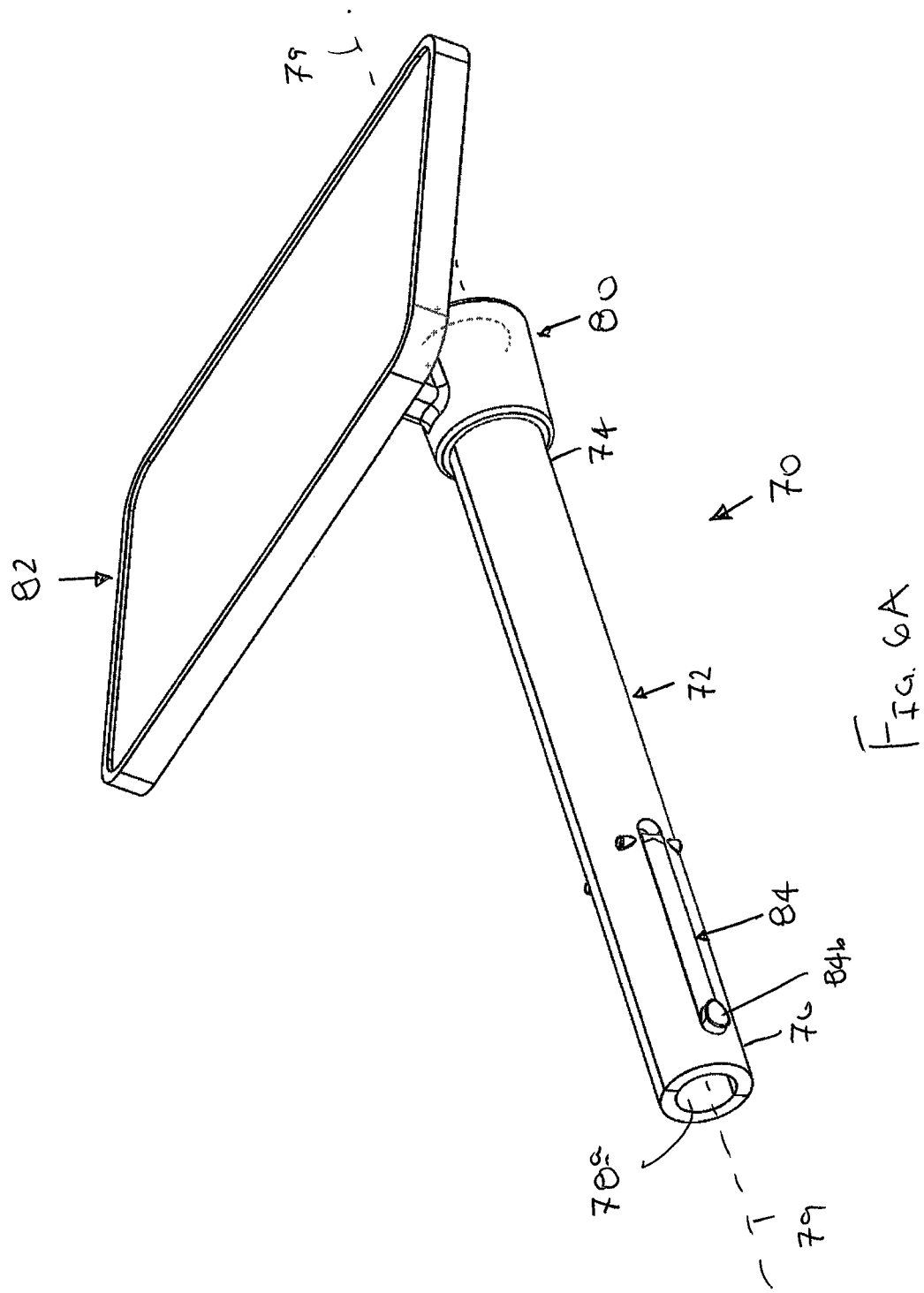

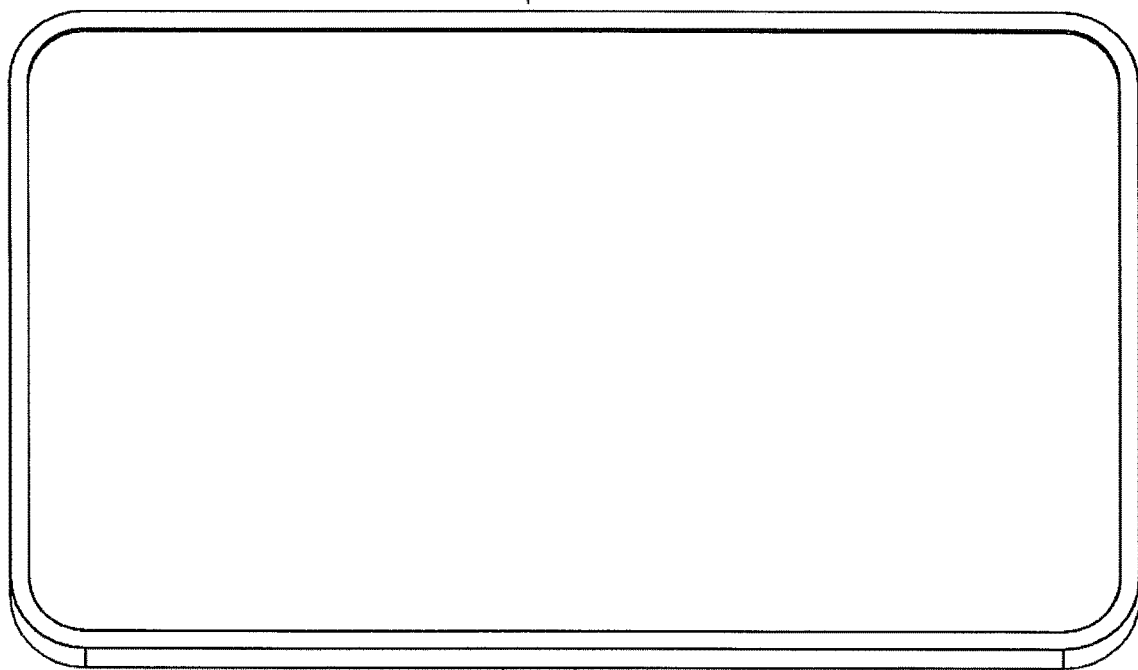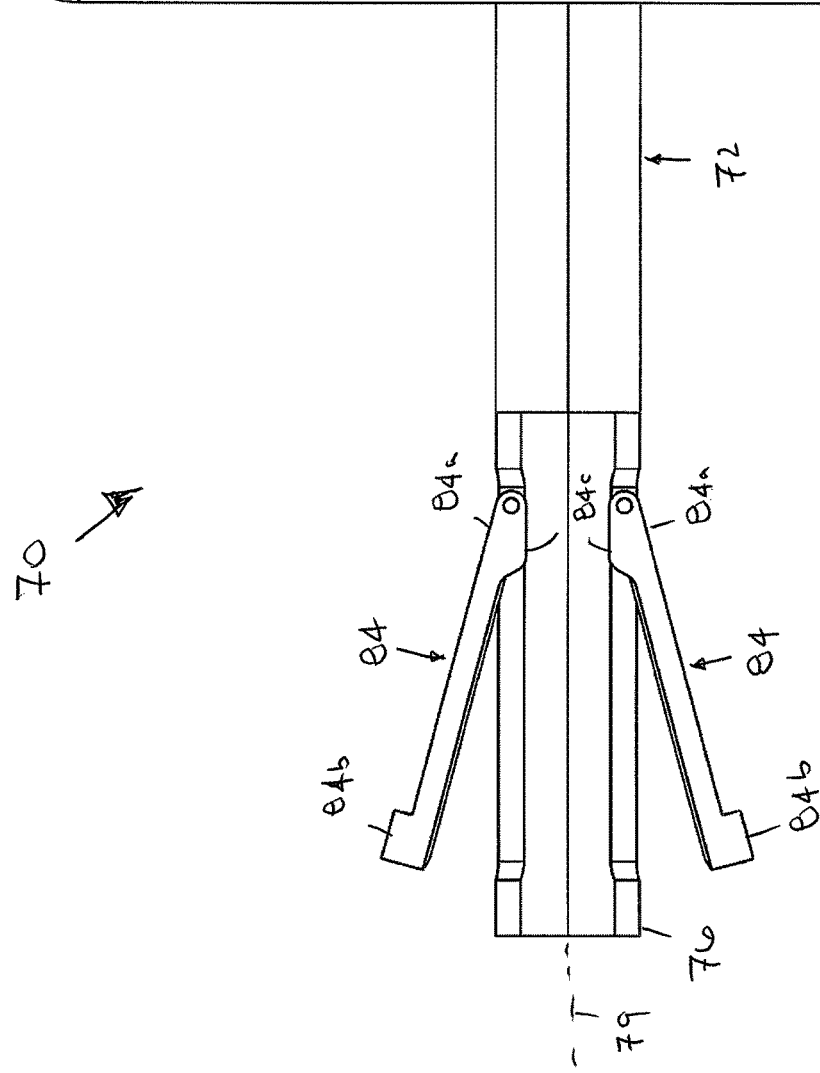
FIG. 6E

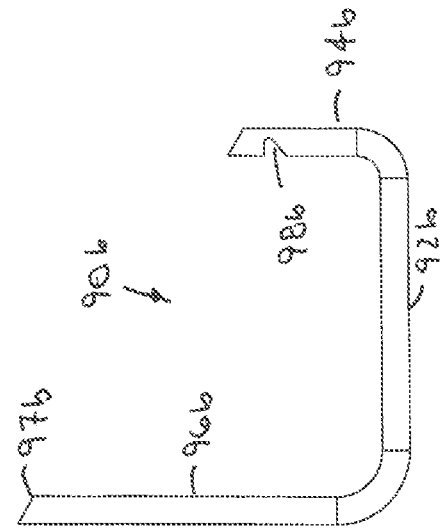
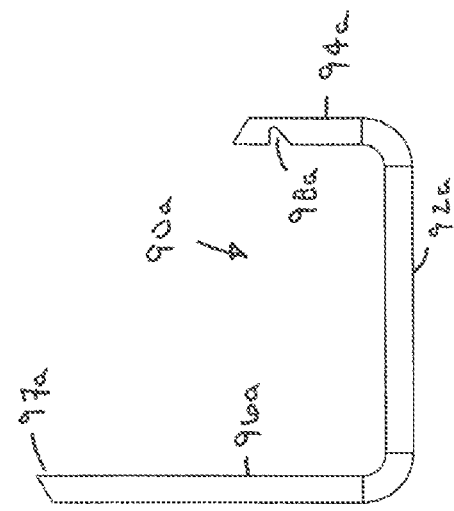
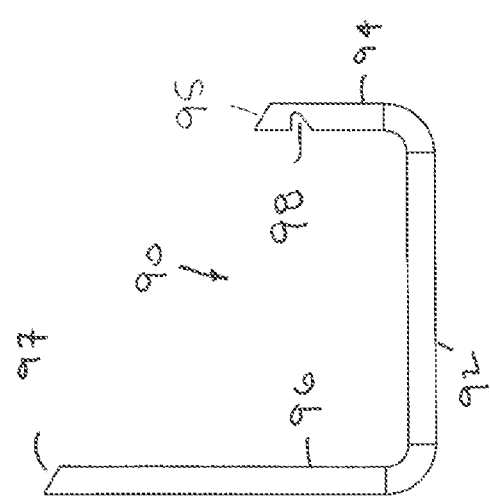
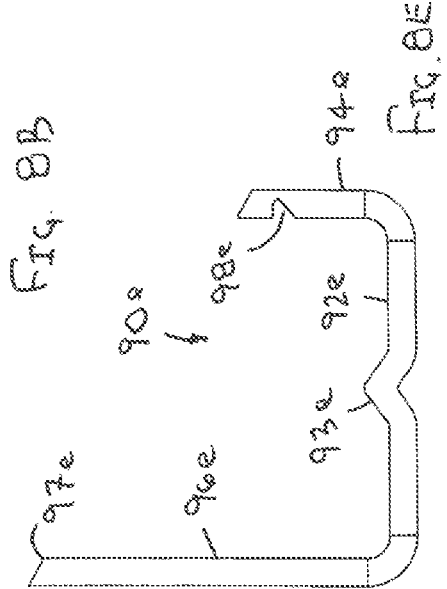
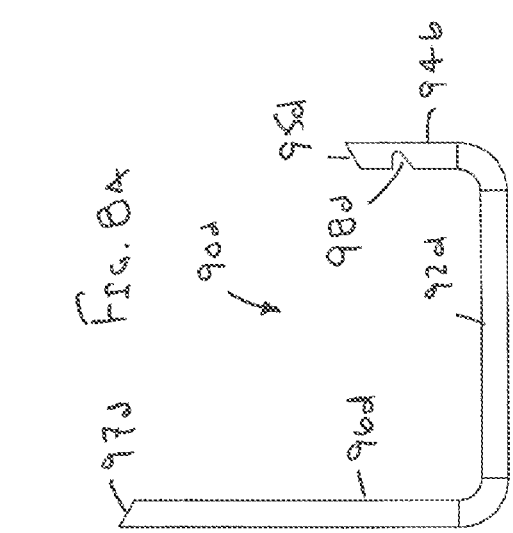
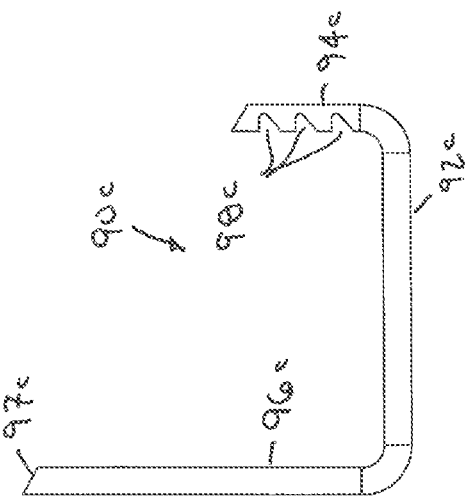

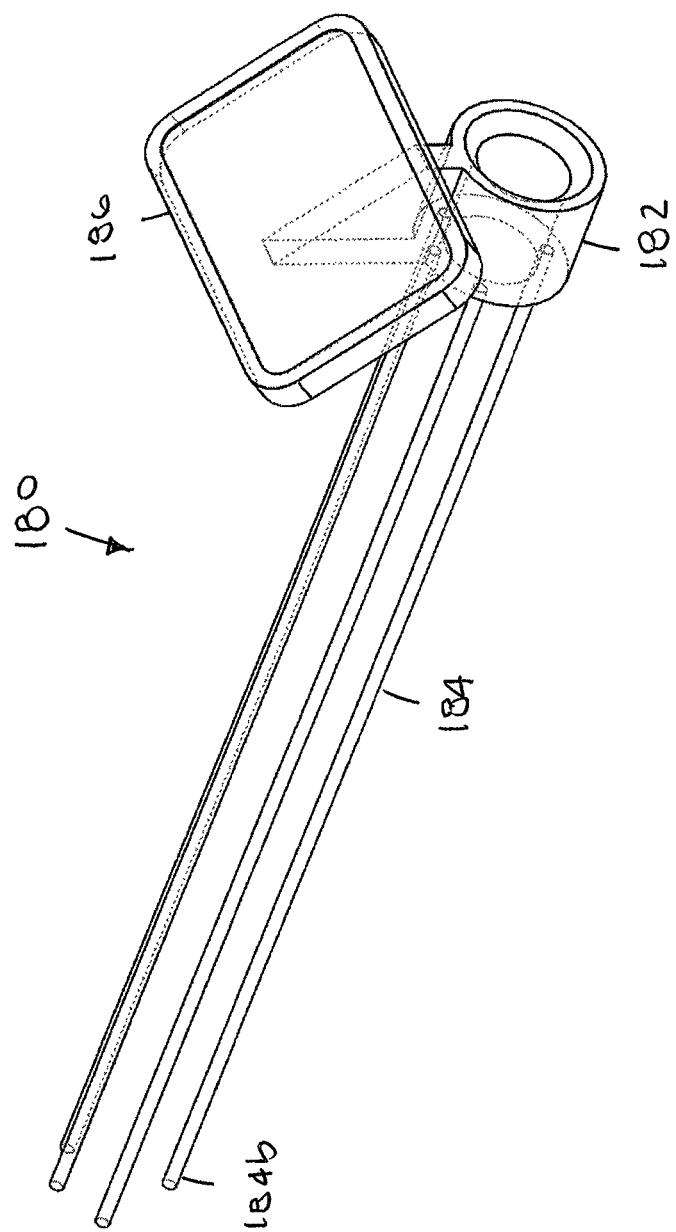

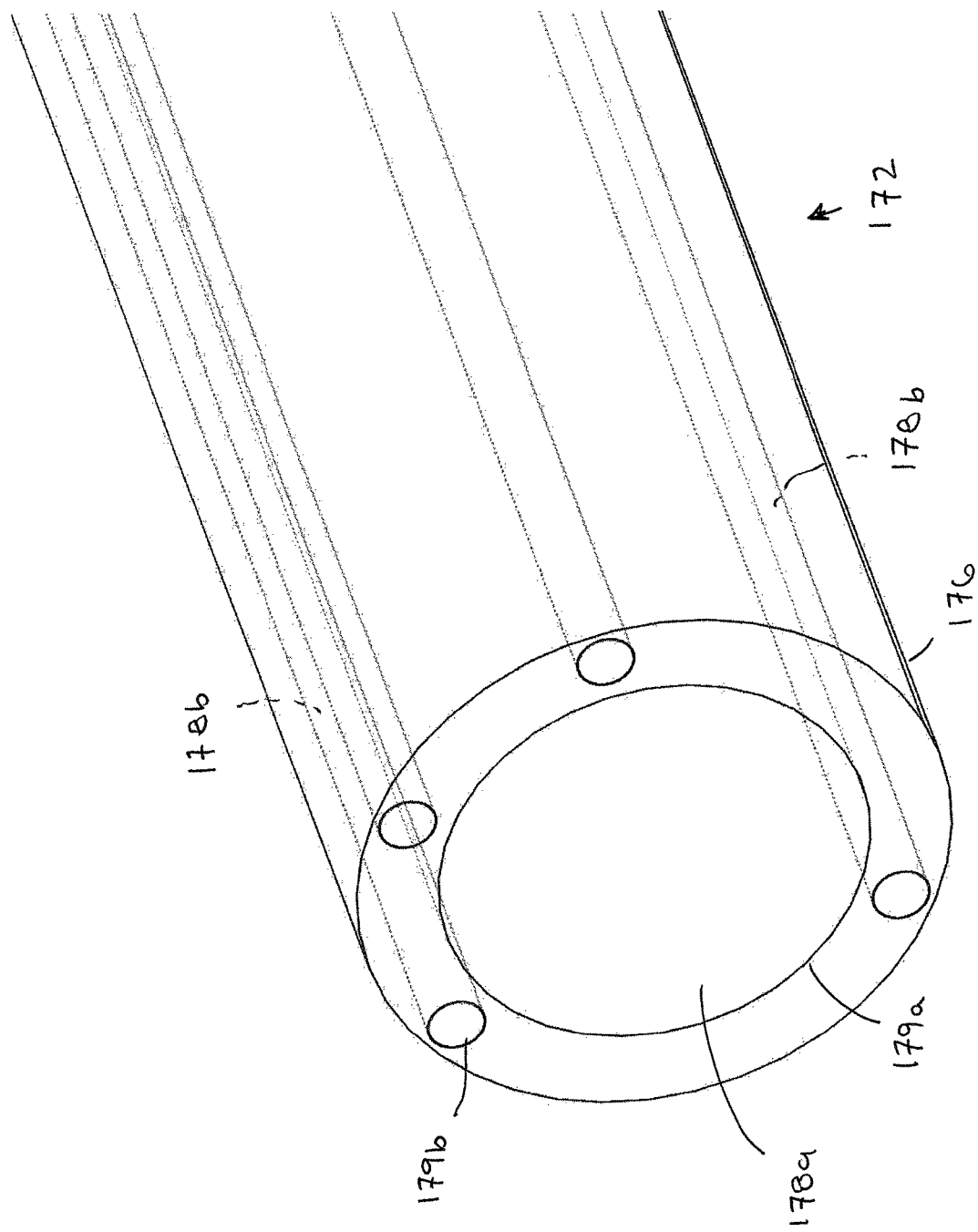

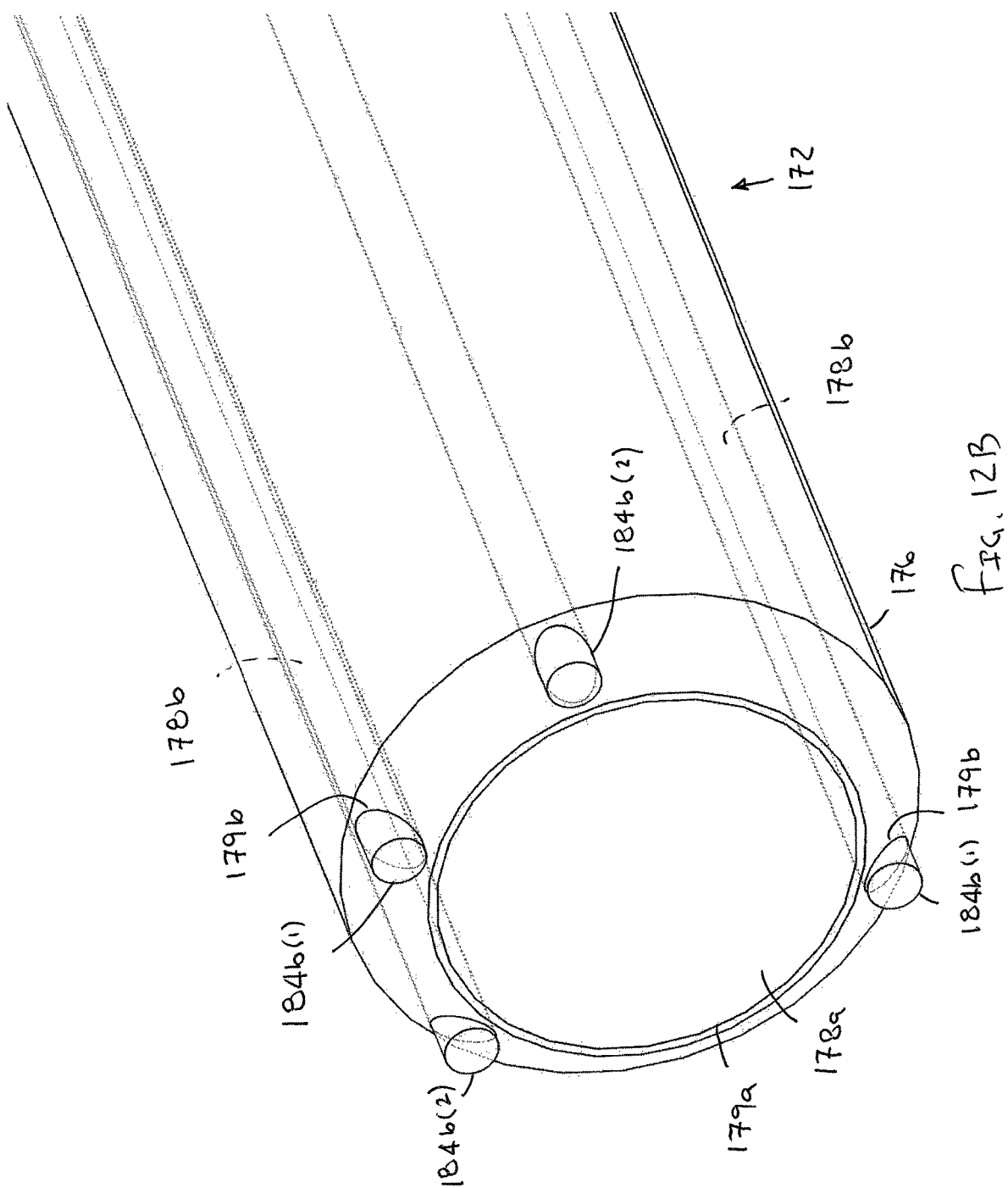

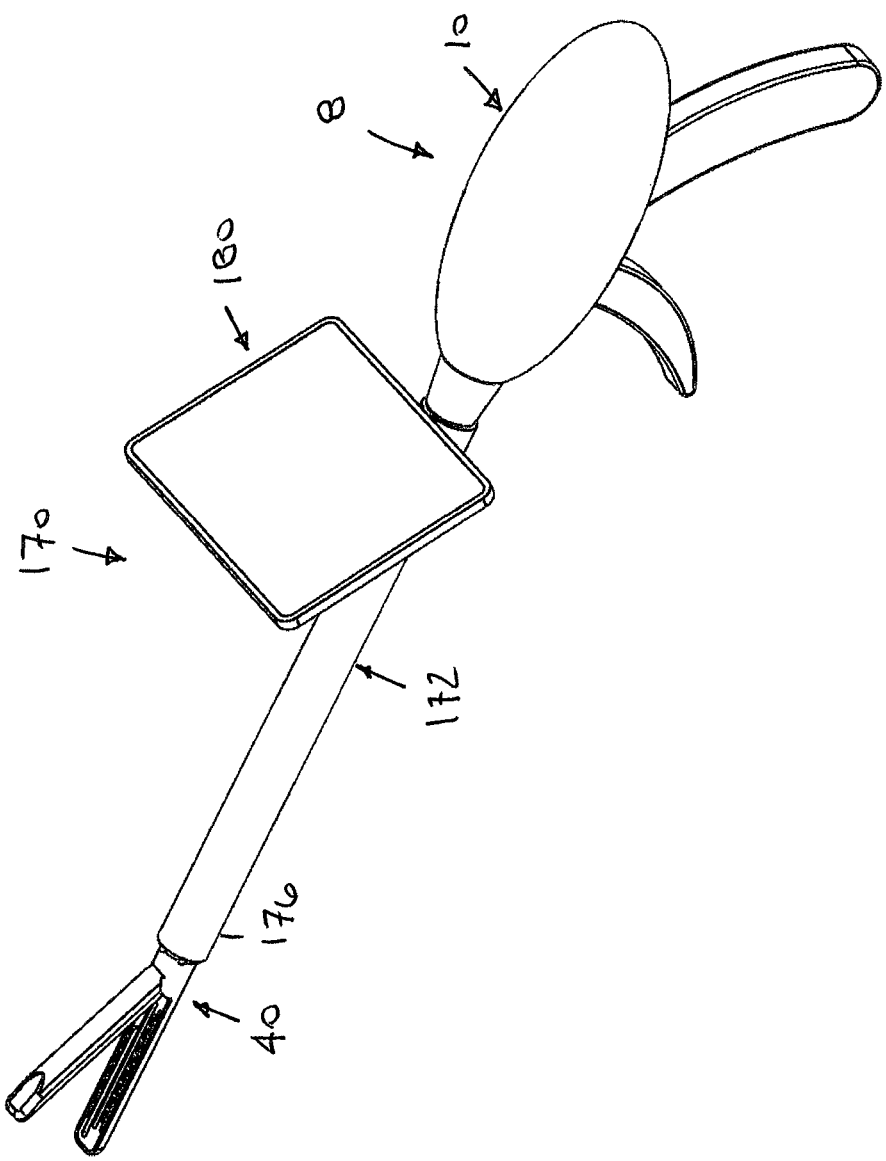

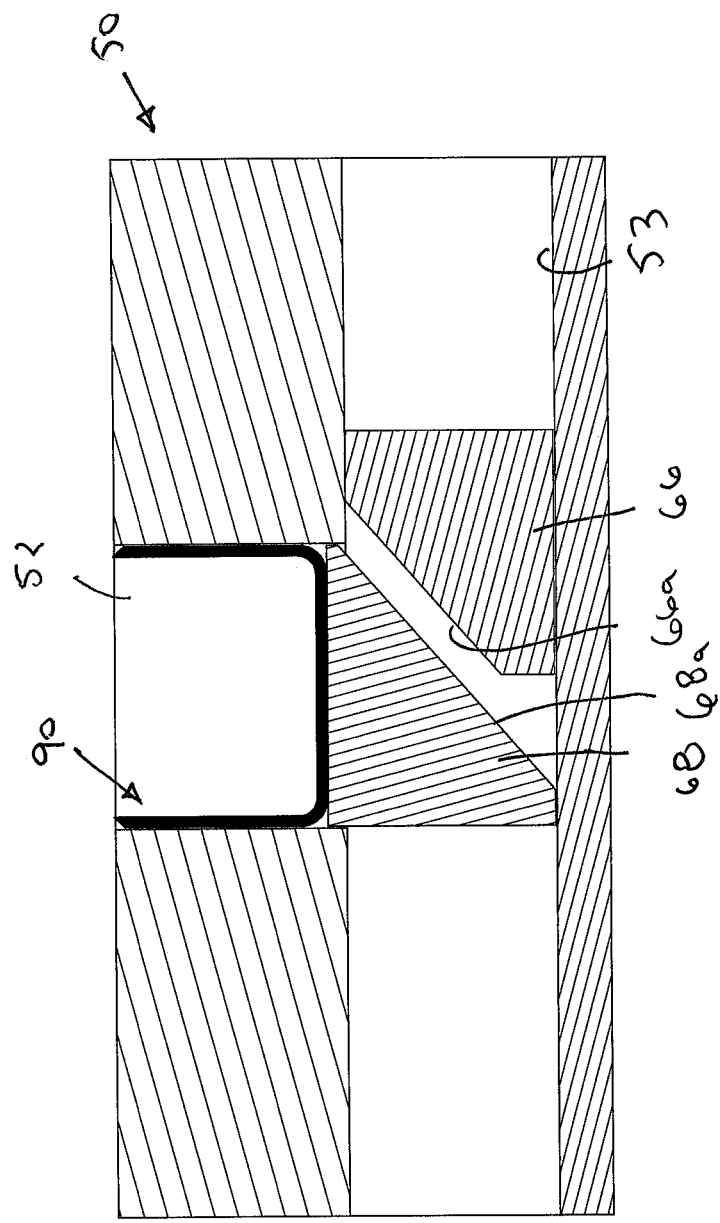

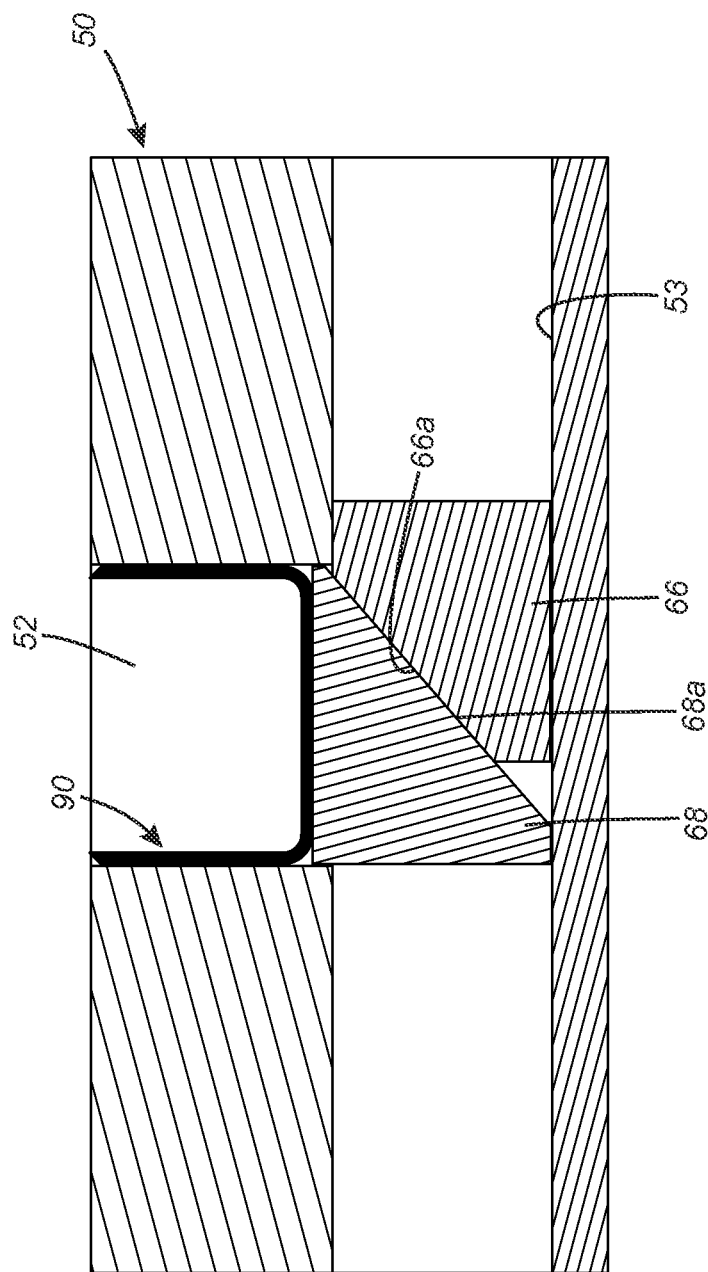

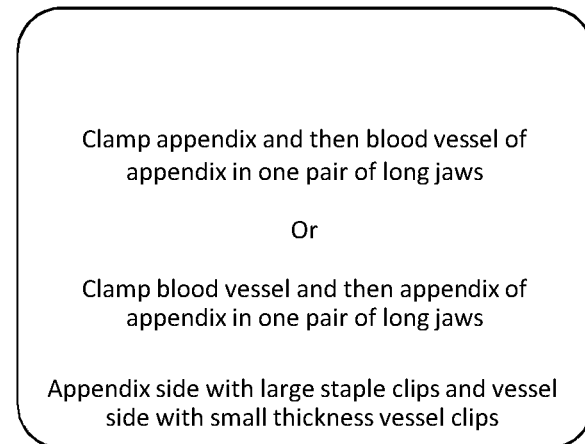
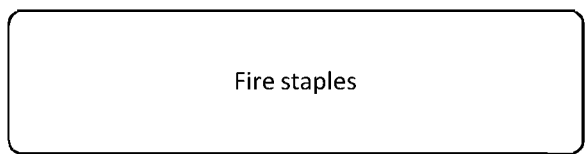
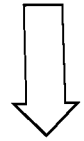
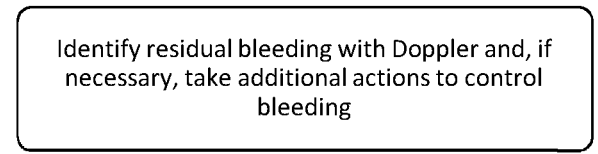
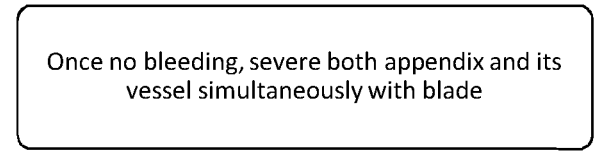
FIG. 16

STAPLER APPARATUS AND METHODS FOR USE

RELATED APPLICATION DATA

The present application claims benefit of U.S. provisional application Ser. No. 62/947,903, filed Dec. 13, 2019, the entire disclosure of which is expressly incorporated by reference herein.

FIELD OF THE INVENTION

The present invention relates generally to apparatus, systems, and methods for performing medical procedures, and, more particularly, to stapler apparatus for performing laparoscopic or other surgery, e.g., to remove an appendix of a subject, and systems and methods for using such apparatus.

BACKGROUND

Appendicitis is seen in approximately 5-10% of the population in their life time. Since 1983, laparoscopic appendix surgery is the mainstay for treatment. In an example of conventional surgery to remove an appendix, the following steps may be performed. First, the appendix and its vessel may be initially identified e.g., lying within a fold of tissue called the mesoappendix. A window or surgical field may be created within the subject's body, and a stapler apparatus is then used, e.g., to initially staple and divide the structure closest to the operator, and then to staple and divide the remaining structure.

For example, FIG. 1 shows exemplary anatomy of an appendix, which may have one of a variety of orientations relative to the intestine, most commonly retrocecal (64%) or pelvic (32%), although less common positions may also be encountered, as shown. An appendicular artery and other blood vessels (not shown) deliver blood to the appendix, whose location relative to the intestine may also vary depending on the orientation of the appendix. The appendix and artery may be separated by fat and/or other tissue. Thus, during a procedure, upon accessing the abdominal cavity, the operator must identify the relative locations of the appendix and vessels before removing the appendix. For example, after identification, the operator may identify the intra-operative manifestation or positioning of the appendix and its vessel, i.e., to identify whether the appendix is closer to the operator and the vessel is positioned further away or vice-versa, and then sequentially staple and divide the closer structure, and then the more distant structure.

To perform laparoscopic or open surgery, a device may be introduced carrying a camera that is independent from the stapler, e.g., to enable visualization of the surgical space and anatomy from the side, e.g., when the stapler is introduced and used to remove the appendix. Existing laparoscopic staplers generally include a cartridge having multiple rows of staples equally distributed on either side of a knife.

One of the most common complications from such surgery is post-operative bleeding. The bleeding is generally sub-clinical in approximately 15%, and clinical in approximately 5% patients, i.e., requiring further intervention. The majority of bleeding occurs from the staple line on individual vessels or vessels within the wall of intestine. For example, "B" shaped clips may create a lumen between the tines that may allow blood or other fluid to escape. Other complication include leaking of intestinal fluid from the intestinal lumen.

Accordingly, apparatus and methods that facilitate laparoscopic surgery, e.g., to remove an appendix would be useful.

SUMMARY

The present invention is directed to apparatus, systems, and methods for performing medical procedures, and, more particularly, to stapler apparatus for performing surgery, such as laparoscopic surgery, e.g., to remove an appendix of a subject or to perform other intestinal procedures, vascular surgery, lung surgery, and the like, and to systems and methods for using such apparatus.

In accordance with an exemplary embodiment, an apparatus is provided for performing a medical procedure that includes a shaft including a proximal end and a distal end sized for introduction into a patient's body; first and second jaws on the distal end of the shaft that are movable relative to one another between open and closed positions, thereby directing first and contact surfaces of the first and second jaws away from and towards one another, respectively, the first jaw carrying one or more staples deployable from the first contact surface; a Doppler radar or other sensor on one of the first and second contact surfaces; and a handle on the proximal end of the shaft comprising a first actuator for opening and closing the jaws, e.g., a trigger to close the second jaw adjacent the first jaw to capture tissue between the contact surfaces, a second actuator for deploying one or more staples from the first jaw into tissue between the first and second contact surfaces, e.g., after locking the jaws closed using the trigger or a separate locking mechanism, and a third actuator for activating the Doppler or other sensor to detect blood flow in the tissue.

In an exemplary embodiment, the first and second jaws may be carried on an end effector removably coupled to the distal end of the shaft. The first jaw may carry first and second sets of staples, e.g., each set arranged in rows adjacent one another, optionally arranged within a replaceable cartridge. A cutting element may be disposed on the distal end, e.g., movable between the first and second sets of staples, e.g., using a fourth actuator on the handle to advance the cutting element to sever the stapled tissue. In addition or alternatively, a thermal element or other hemostasis element may also be provided on one of the first and second jaws, e.g., opposite the Doppler sensor, and the handle may include a fifth actuator for activating the hemostasis element to deliver thermal energy to the stapled tissue. Optionally, the handle may include one or more additional actuators, e.g., one or more controls for positioning and/or activating a light and/or camera carried on the distal end of the shaft or the end effector.

In accordance with another embodiment, an end effector is provided for a stapler apparatus including a shaft including a proximal end including a handle and a distal end sized for introduction into a patient's body. The end effector may include one or more connectors for removably connecting the end effector to the distal end of the shaft and, optionally, a cartridge insertable into a recess of one of the jaws. The first and second jaws are movable relative to one another between open and closed positions, thereby directing contact surfaces of the first and second jaws away from and towards one another, respectively. For example, the first jaw may be fixed and the second jaw may be pivotally mounted to open and close relative to the first jaw, e.g., to capture tissue between the contact surfaces. One or more staples are carried by the first jaw, e.g., in a replaceable cartridge, such that actuation of a staple actuator on the handle deploys one or more staples from the first jaw into tissue between the contact surfaces and towards the second jaw to deform the one or more staples. Optionally, a Doppler radar sensor and/or hemostasis element may be provided on one of the contact surfaces to detect blood flow in the tissue.

In accordance with still another embodiment, a method is provided for performing a surgical procedure within a patient's body that includes introducing first and second jaws on a distal end of a shaft into a region within the patient's body; with the jaws in an open position, placing tissue within the region between contact surfaces of the first and second jaws; closing the jaws to engage the tissue; actuating a staple actuator to deploy one or more staples from the first jaw into the tissue towards the second jaw to deform the one or more staples and secure the tissue. For example, the second jaw may be closed to squeeze the tissue between the contact surfaces and, optionally, may be locked in the closed position. The staple(s) may be then be deployed from the first jaw using the staple actuator such that they are directed through the tissue and engage anvils or shaping surfaces on the second jaw to deform tines of the staple(s). A Doppler or other sensor on one of the contact surfaces may be activated to detect blood flow in the stapled tissue; and after confirming that blood flow has discontinued in the stapled tissue, a cutting element may be actuated to sever the stapled tissue from adjacent tissue at the region.

In accordance with yet another embodiment, a method is provided for performing an appendectomy within a patient's body that includes introducing first and second jaws on a distal end of a shaft into an abdominal cavity of the patient's body; placing an appendix and appendicular artery within the abdominal cavity between contact surfaces of the first and second jaws; actuating one or both of the first and second jaws to secure the appendix and artery between the contact surfaces; and deploying one or more staples from the first jaw through the appendix and artery to staple the appendix and artery. Thereafter, a Doppler sensor on one of the contact surfaces may be activated to detect blood flow in the stapled appendix and artery, and, if blood flow is detected, a thermal element may be activated to deliver thermal energy to stop blood flow, e.g., alternately to detect and cauterize the tissue. Once blood flow ash stooped, a cutting element may be actuated to simultaneously sever the appendix and artery.

In accordance with another embodiment, an apparatus is provided for performing a medical procedure that includes a shaft including a proximal end, a distal end sized for introduction into a patient's body, and a longitudinal axis extending between the proximal and distal ends; first and second jaws on the distal end of the shaft that are movable relative to one another between open and closed positions, thereby directing first and contact surfaces of the first and second jaws away from and towards one another, respectively, the first jaw carrying first and second sets of staples positioned on opposite sides of a cutting element, wherein at least some of the staples are a different size than other staples; and a handle on the proximal end of the shaft. For example, each set of staples may include one to five rows of staples aligned along the longitudinal axis, with two to fifty staples in each row. The staples in each set and/or each row may have different sizes depending on the anatomy encountered. For example, the apparatus may include a plurality of available cartridges, each including different arrangements of staples, that may be selected and inserted into a cavity of the first jaw. The handle includes a first actuator for driving the staples from the first jaw into tissue between the first and second contact surfaces and towards the second jaw to deform the staples; and a second actuator for advancing the cutting element from a retracted position to an advanced position aligned with the longitudinal axis to sever the stapled tissue.

In accordance with yet another embodiment, an end effector is provided for a stapler apparatus including a shaft comprising a proximal end including a handle, a distal end sized for introduction into a patient's body, and a longitudinal axis extending between the proximal and distal ends. The end effector may include one or more connectors for removably connecting the end effector to the distal end of the shaft; first and second jaws that are movable relative to one another between open and closed positions using a first actuator on the handle, thereby directing first and contact surfaces of the first and second jaws away from and towards one another, respectively; and a cartridge carried by the first jaw comprising first and second sets of staples arranged in rows on opposite sides of a cutting element such that actuation of a second actuator on the handle deploys the staples into tissue between the first and second contact surfaces and drives the staples against the second jaw to deform the one or more staples, wherein at least some of the staples are a different size than other staples.

In accordance with still another embodiment, a staple is provided for delivery into tissue that includes a substantially straight base element including first and second ends; a first tine extending from the first end substantially perpendicular to the base, the first tine having a first length and including one or more notches adjacent a tip of the first tine; and a second tine extending from the second end substantially perpendicular to the base to a second tip, the second tine having a second length longer than the first length and longer than the length of the straight base such that, when the second tine is bent adjacent the base, the second tip of the second tine is engaged in the one or more notches located on the first tine.

In accordance with another embodiment, a port is provided for introducing one or more instruments into a patient's body that includes an elongate tubular member comprising a proximal end, a distal end sized for introduction into a patient's body, and a lumen extending between the proximal and distal ends, thereby defining a longitudinal axis there between; a display; and one or more deployment arms on the tubular member adjacent the distal end carrying an imaging device, each deployment arm comprising a first end pivotably coupled to the tubular member and a second free end that is movable from a retracted position wherein the second end is aligned with a wall of the tubular member and a deployed position wherein the second end moves outwardly relative to the longitudinal axis for presenting images on the display.

In accordance with still another embodiment, a port is provided for introducing one or more instruments into a patient's body that includes an elongate tubular member comprising a proximal end, a distal end sized for introduction into a patient's body, and a primary lumen extending between the proximal and distal ends for receiving an instrument therethrough, and a plurality of secondary lumens positioned around the primary lumen and extending between the proximal and distal ends; and a video module. The video module may include a hub; a display; and a plurality of elongate imaging elements mounted to the hub and sized for introduction simultaneously into respective secondary lumens of the tubular member such that distal tips of the imaging elements are positioned adjacent the distal end of the tubular member for acquiring images beyond the distal end.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 2A is a side view of an exemplary embodiment of a stapler apparatus including a reusable portion including a shaft extending from a handle and a disposable end effector coupled to the shaft.

FIGS. 2B and 2C are side and perspective views, respectively, of the apparatus of FIG. 2A with a display on the reusable portion.

FIGS. 3A and 3B are perspective and side views, respectively, of an exemplary embodiment of an end effector that may be coupled to the shaft of the apparatus of FIG. 2A, the end effector including a first jaw carrying a plurality of staples within a cartridge and a second jaw pivotable relative to the first jaw between an open position (FIG. 3A) and a closed position (FIG. 3B).

FIG. 3C is a cross-sectional view of the end effector of FIGS. 3A and 3B with the jaws spaced apart.

FIGS. 5A-5C are cross-sectional views showing alternative embodiments of jaws and cartridges including a Doppler sensor and/or thermal element at different locations on the jaws.

FIGS. 6A and 6B are perspective views of an exemplary embodiment of an access port including a deployable imaging system carried on deployment arms in retracted and deployed configurations, respectively.

FIGS. 6D and 6E are top views of the access port of FIGS. 6A and 6B, respectively, with a portion of the tubular shaft removed to show details of the deployment arms of the imaging system.

FIG. 7C is a side view of the staple of FIGS. 7A and 7B.

FIGS. 8A-8E are side views of alternative embodiments of staples or clips that may be delivered using the stapler apparatus herein.

FIG. 11 is a perspective view of a video module that includes elongate imaging sleeves receivable in corresponding lumens of the tubular member.

FIGS. 12A and 12B are details of the distal end of the tubular member of FIG. 10 before and after inserting the imaging sleeves of the video module into secondary lumens of the tubular member.

FIG. 13A is a perspective view of the access port of FIGS. 9A-9C with a stapler apparatus inserted through a primary lumen of the tubular member.

FIGS. 15A-15D are details showing a wedge actuation mechanism for deploying a staple from a cartridge received in a jaw of an end effector.

FIG. 16 is a flowchart showing an exemplary method for using the apparatus herein to perform an appendectomy.

DETAILED DESCRIPTION OF THE EXEMPLARY EMBODIMENTS

Figure 1:
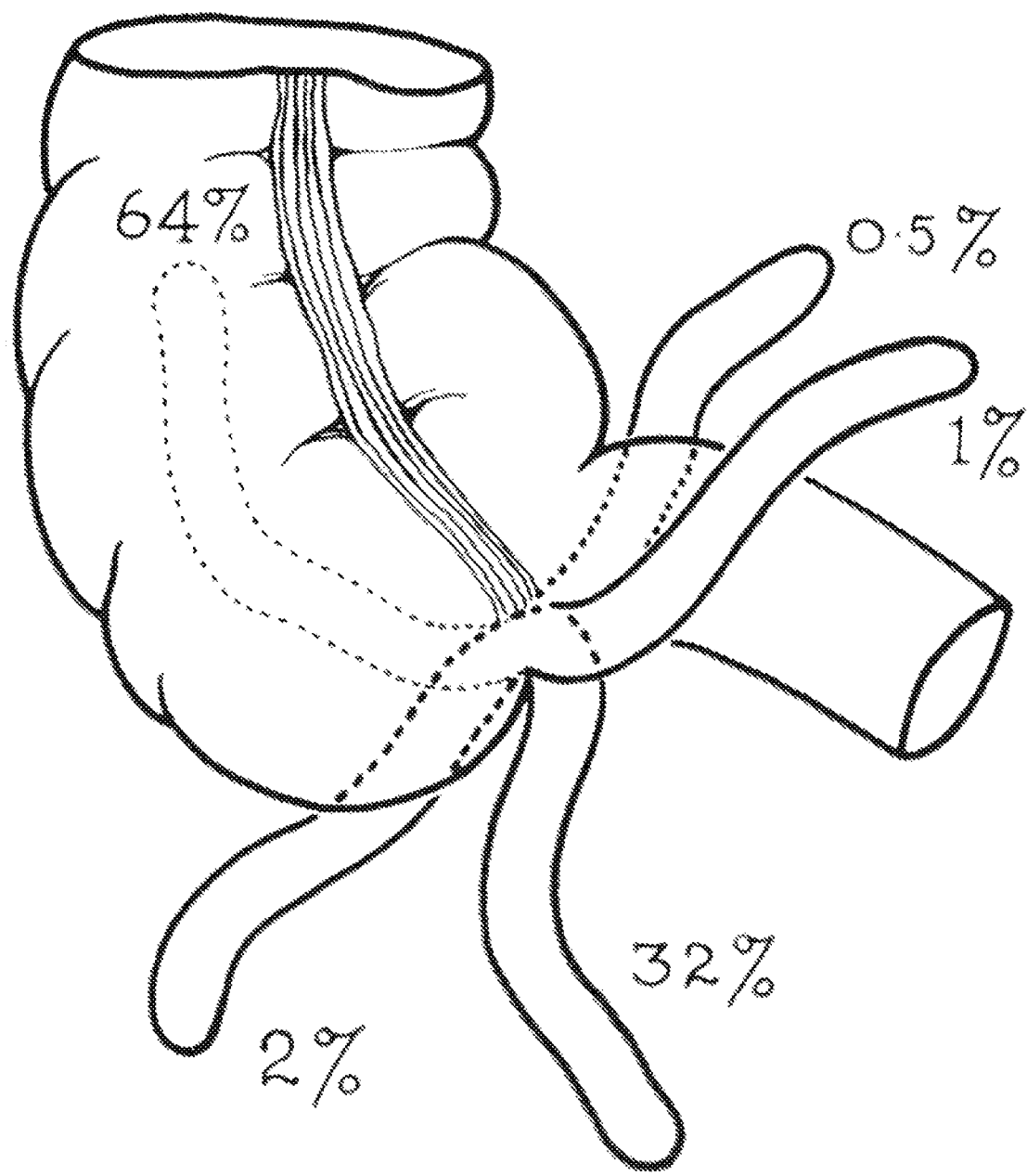
FIG. 1 is a detail showing exemplary anatomy of an appendix, which may have a variety of orientations relative to the intestine.

Before the exemplary embodiments are described, it is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Turning to the drawings, FIG. 2A shows an exemplary embodiment of a stapler apparatus 8 that may be used during a medical procedure, e.g., during laparoscopic surgery to remove a patient's appendix (not shown). Generally, the apparatus 8 includes a reusable shaft/handle portion or handpiece 10 including a shaft 20 and a handle 30, and a disposable, single-use portion or end effector 40, e.g., configured to receive a single-use cartridge (not shown), which may be removably coupled to the shaft 20 before or during a procedure, as described further below. Alternatively, at least some of the components of the end effector 40 may be permanently incorporated into the reusable portion 10, e.g., such that the entire apparatus 8 may be single-use or may be cleaned between procedures and reused.

As shown, the shaft 20 is an elongate member, e.g., a substantially rigid tubular body, including a proximal end 22 and a distal end 24, defining a longitudinal axis 26 extending there between. The shaft 20 may include one or more lumens or passages (not shown) extending between the proximal and distal ends 22, 24, e.g., for receiving actuator elements, wires, and/or other components, as described elsewhere herein. At least the distal end 24 of the shaft 20 is sized for introduction into a patient's body, e.g., having a diameter sufficiently small enough to be received through a port or cannula to allow introduction into a laparoscopic surgical space within a patient's body.

Optionally, at least a portion of the shaft 20 may be malleable, e.g., such that at least a distal region of the shaft 20 may be deformed into a desired shape outside the patient's body, which the shaft 20 may maintain during introduction. Alternatively, at least a distal region of the shaft 20 and/or the end effector 40 may be flexible, e.g., for introduction into body passages, such as blood vessels, GI passages, and the like, such that the distal region follows the passages during introduction. Optionally, in this alternative, the shaft 20 may include one or more steering wires or other elements therein (not shown) that may be actuated to change the shape of the shaft 20, e.g., to facilitate introduction into a desired location and/or manipulation within the patient's body.

The handle 30 may include a handgrip 32, e.g., shaped and/or otherwise configured to facilitate holding and/or manipulating the apparatus 8 during use. In addition, the handle 30 may include one or more actuators, e.g., for operating mechanical and/or electrical components on the stapler assembly 40. For example, a trigger or other jaw actuator 34 may be provided, e.g., adjacent the handgrip 32, that may be pulled or otherwise actuated to jaws 46, 47 and a separate actuator (not shown) may be provided to subsequently deploy one or more staples (not shown) from the stapler assembly 40. For example, the trigger 34 may be pulled to close the second jaw 48 immediately adjacent the first jaw 46 to engage tissue between contact surfaces 46a, 48a, e.g., as described further elsewhere herein. Optionally, the trigger 34 may include a ratchet mechanism to allow the second jaw 48 to move towards the first jaw 46 while preventing opening, e.g., to squeeze tissue between the jaws 46, 48, e.g., until a release mechanism is actuated. Alternatively, a separate locking mechanism may be provided on the handle 30, which may be selectively activated to lock and release the second jaw 48, as described elsewhere herein. In addition or alternatively, several other actuators may be included on the handle 30 or shaft 20 10 to achieve independent actuation of various functions/parts of the end effector, such as a staple actuator that be advanced to deploy one or more staples and/or retracted, a cutting actuator for blade actuation (forward and backward), a Doppler sensor trigger, an electrical cautery power switch, and/or an actuator for controlling end effector orientation.

Optionally, as shown in FIGS. 2B and 2C, a display or other output device 38 may be provided on the handle 30, e.g., to facilitate observing or otherwise monitoring the procedure. For example, a camera, light, and/or other imaging device (not shown) may be provided on the stapler assembly 40 and/or the distal end 24 of the shaft 20 that may be used to acquire images of a surgical space into which the stapler assembly 40 is introduced, as described further elsewhere herein. In one embodiment, a display 38 may be removably mounted on the handle 30, which may include one or more connectors or cables (not shown) that may be coupled to corresponding connectors on the handle 30, which are, in turn, coupled to one or more wires extending to the imaging device on the stapler assembly 40. Alternatively, the display 38 may be permanently mounted to the handle 30 and one or more wires or other elements may communicate with the imaging device. In another alternative, a display (not shown) may be provided that is separate from the apparatus 8, and the apparatus 8 may include a communications interface, e.g., a wireless transmitter, that may transmit signals from the imaging device wirelessly, e.g., using Bluetooth or other communications protocols, to allow images to be presented on the display.

For example, a CMOS, CCD, or other imaging element (not shown) may be provided on the distal end 24 of the shaft 20 (or alternatively on the end effector 40) that is oriented to acquire images of the region beyond the stapler assembly 40 and/or between jaws 46, 48 of the end effector 40. One or more wires and/or optical fiber may transmit signals to the display 38, which may include a processor to process the signals and present the images on a screen of the display 38. In addition or alternatively, one or more LEDs or other light sources may be provided on the distal end 24 of the shaft 20 (or alternatively on the end effector 40), e.g., adjacent the imaging element to provide illumination for the images. For example, one or more lights may be arranged circumferentially on the distal end 24 of the shaft 20, such as a circular Xenon LED lamp (not shown), e.g., operating at 200-2500 W, that may provide dispersed illumination (due to internal reflections in the lamp) without generating thermal energy that may damage nearby tissue. Alternatively, one or more LEDs or other light sources (not shown) may be provided in the handle 30, and light may be transmitted using light conductive material such as optical fiber or transparent plastic to provide illumination to the distal end 24. The handle 30 and/or display 38 may include one or more controls (not shown), e.g., to turn the illumination source(s) and/or imaging element(s) off and on, as desired. Optionally, the imaging element(s) and/or illumination source(s) may be movable relative to the end effector 40, e.g., rotated about the longitudinal axis 26 and, if so, one or more actuators (not shown) may be provided on the handle 30 to rotate or otherwise adjust their position during a procedure.

Returning to FIG. 2A, generally, the end effector 40 on the distal end 24 of the shaft 20 includes first and second jaws 46, 48 carrying one or more staples (not shown) and, optionally, one or more additional components for use during a procedure. For example, as shown in FIGS. 3A-3C, the end effector 40 may include a removable cartridge 50 receivable within a recess, track, or other cavity 46c within the first jaw 46. The end effector 40 may also include a tubular housing 42 from which the first jaw 46 extends that includes a proximal end 44 that may be connected to the distal end 24 of the shaft 20, e.g., using one or more detents, latches, sockets, threads and/or other connectors (not shown) on the proximal end 44 of the housing 40 and/or the distal end 24 of the shaft 20. When the end effector 40 is mechanically connected to the shaft 20 by the connector(s), additional connectors may automatically engage, e.g., to mechanically couple actuatable components on the end effector 40 with actuator elements in the shaft 20 and/or electrically couple electrical components on the end effector 40 with corresponding wires in the shaft 20 (not shown), as will be appreciated by those skilled in the art. For example, a wedge mechanism (not shown, see, e.g., FIGS. 15A-15D) may be provided within the housing 42 adjacent the first jaw 46 that may be coupled to an actuator shaft (also not shown) within the shaft 20 such that actuation of a staple actuator on the handle 30 may be activated to advance and retract the actuator shaft and wedge to deliver the staples, as described elsewhere herein.

As shown, the first jaw 46 may be integrally formed with or otherwise fixed relative to the housing 42, e.g., such that the first jaw 46 remains aligned with the axis 26 of the shaft 20 during use. The second jaw 48 may be movably mounted to the housing 42, e.g., by one or more hinges or other features (not shown) such that the second jaw 48 may be pivotable between an open position, e.g., as shown in FIG. 3A, and a closed position, e.g., as shown in FIG. 3B. In the open position, contact surfaces 46a, 48a of the jaws 46, 48 may be spaced apart from one another, e.g., to allow a tissue structure to be positioned between the jaws 46, 48, e.g., on the first contact surface 46a, while in the closed position, the contact surfaces 461, 48b may be immediately adjacent one another, e.g., substantially parallel to one another, as shown in FIG. 3B. For example, in the closed position, the contact surfaces 46a, 48a may have sufficient clearance between them to squeeze, secure, and/or otherwise engage tissue positioned between the jaws 46, 48.

The jaws 46, 48 may be biased to one of the open and closed positions or may be actuatable between the open and closed positions. For example, the jaws 46, 48 may be provided initially in a closed position, e.g., to facilitate introduction into a patient's body, whereupon a lock or other mechanism may be released, whereupon the second jaw 48 may automatically move to the open position, and the actuator 34 on the handle 30 may become active to deploy staples and/or close the second jaw 48, as described further elsewhere herein. Alternatively, the trigger 34 on the handle 30 may be pulled or released to close and open the second jaw 48 without deploying staples to facilitate introduction and/or manipulation of the cartridge 40, e.g., until a switch or other control is actuated to activate deployment of the staples. A locking mechanism, e.g., a ratchet or other lock (not shown), may be provided to prevent the second jaw 48 from opening until released.

With particular reference to FIG. 3A, the first jaw 46 may receive a disposable cartridge 50 which may be received in cavity 46c of the first the jaw 46 such that an exposed surface 50a of the cartridge 50 defines the first contact surface 46a. The cartridge 50 may carry a plurality of staples (not shown), e.g., in arranged in a plurality of rows aligned with the axis 26 of the shaft 20. For example, in the embodiment shown, the contact surface 50a of the cartridge 50 includes recesses or receptacles 52 arranged in three rows 52a, 52b, 52c from which staples may be deployed simultaneously and/or in rapid succession.

Figure 5C:
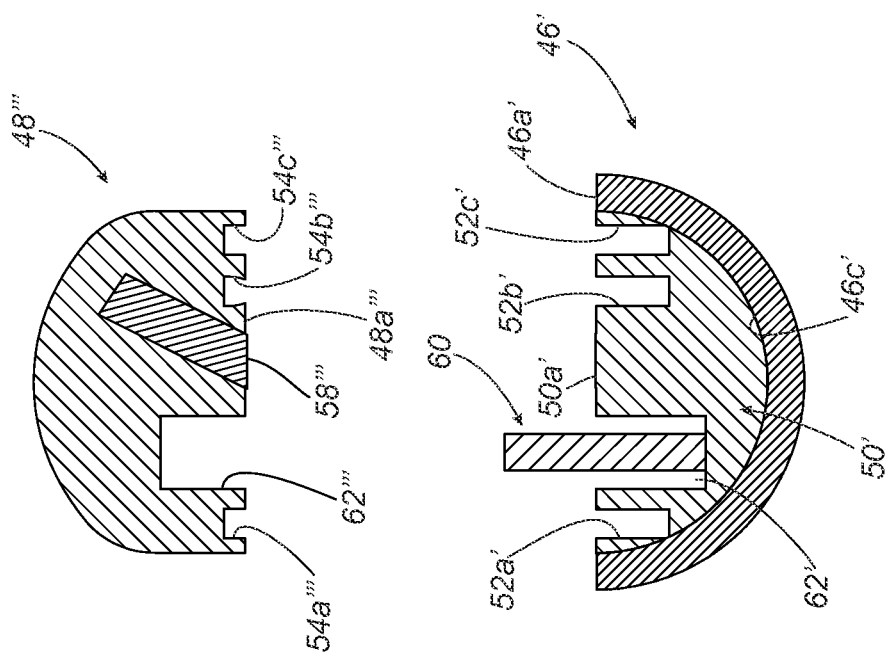

Optionally, the cartridge 50 or first jaw 46 may include a thermal element 56 on the first surface 46a adjacent the rows of staples. For example, the cartridge 50 may include sets of staples disposed on opposite sides of the thermal element 56, e.g., with the sets aligned with the axis 26 of the shaft 20. Alternatively, as shown in FIGS. 5A-5C, the thermal element may be omitted from the jaws/cartridge, if desired. If the staples are carried by a cartridge 50 that is removable from the first jaw 46, the thermal element 56 may be mounted on an exposed surface of the cartridge 50, e.g., if the cartridge 50 provide the first contact surface 46a. Alternatively, the thermal element 56 may be permanently mounted on the first jaw 46 and the cartridge 50 may define the portions of the first contact surface 46a on either side of the thermal element 56 (not shown).

Figure 4A:
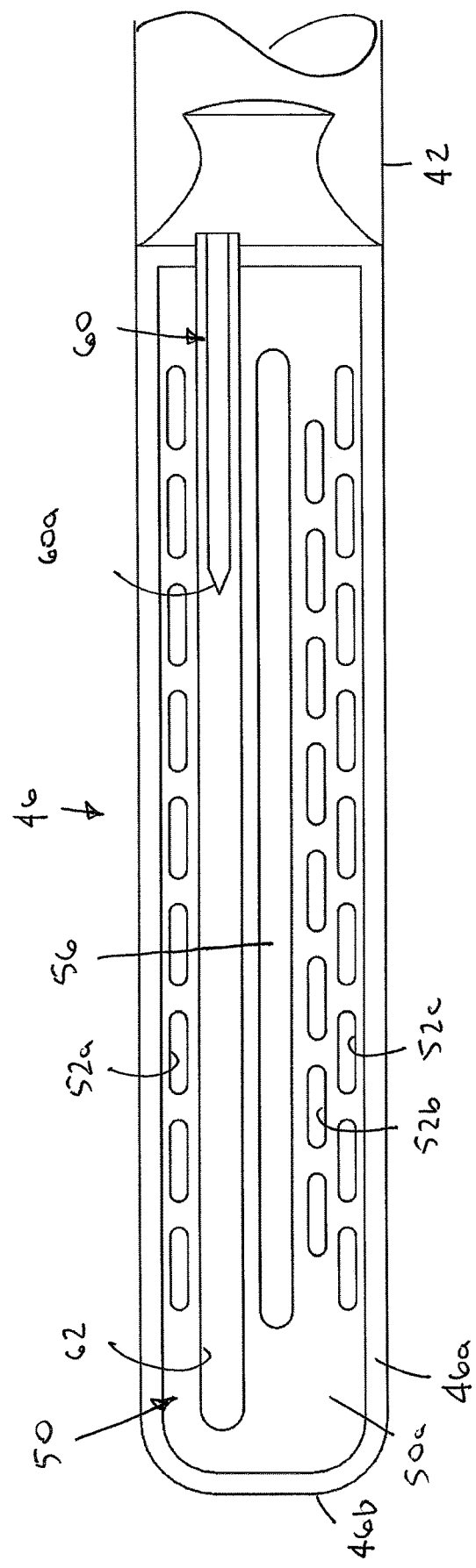
FIG. 4A is a top view of the first (bottom) jaw of the end effector shown in FIGS. 3A and 3B with a cartridge carrying staples received in a cavity of the jaw.

In the example shown in FIGS. 3A and 4A, a first row or set of staple receptacles 52a may be located on the right side of the thermal element 56 (from the perspective of a user holding the handle 30 of the apparatus 8), and second and third rows or sets of staple receptacles 52b, 52c may be located on the left side of the thermal element 56. For example, in this configuration, the first set of staples may be delivered into the appendix being removed, while the second set of staples may be delivered into the intestine and remain within the patient's body after the appendix is removed. Alternatively, the arrangement of the receptacles 52 may be reversed if desired, e.g., with the first set on the left and the second set on the right for approaches where the appendix is on the left (from the perspective of the operator of the apparatus 8) and the intact intestine is on the right. As shown, the second set of receptacles 52b, 52c may include two rows of staples that are staggered relative to one another along the axis 26, e.g., to enhance stapling a tissue structure captured in the jaws 46, 48, as described elsewhere herein.

In the embodiment shown in FIGS. 3A and 4A, the receptacles 52 have similar dimensions, e.g., having the same length aligned with the axis 26, and the staples deployable from the receptacles 52 may have the same dimensions. Alternatively, the dimensions of the receptacles and, consequently, the staples, may be varied along each row and/or in different rows, as described further elsewhere herein.

Figure 4B:
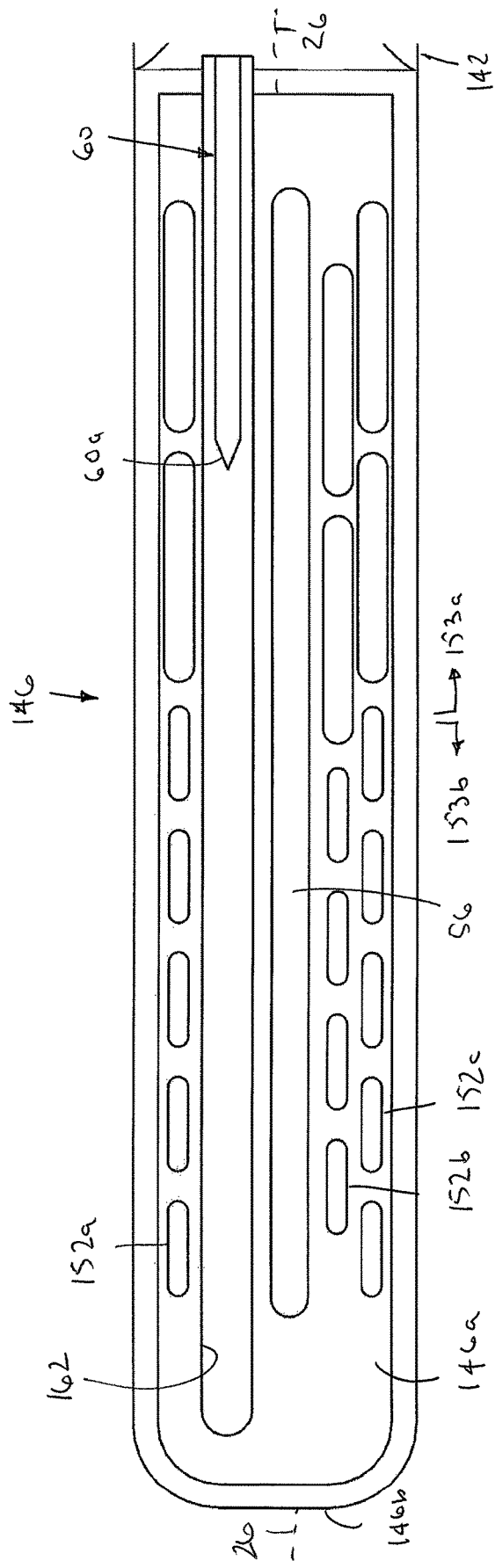
FIGS. 4B and 4C are top views of alternative embodiments of first jaws and cartridges that may be provided that include different size staples and receptacles.

For example, FIG. 4B shows an alternative embodiment of a first jaw 146 (generally similar to jaw 46) except that the rows of staple receptacles 152 include a first or proximal set of receptacles 153a and a second or distal set of receptacles 153b that have different sizes. For example, as shown, the first two receptacles in each row 152 (in the proximal set 153a) are larger than the remaining five receptacles (in the distal set 153b). In this alternative, when the staples are deployed, the larger, proximal staples will be deployed first followed by the smaller, distal staples, e.g., as the staple actuator (e.g., a piston and/or sledge, not shown) advances and the pushes the staples against the second jaw 48 (also not shown) to deform the deployed staples.

Figure 4C:
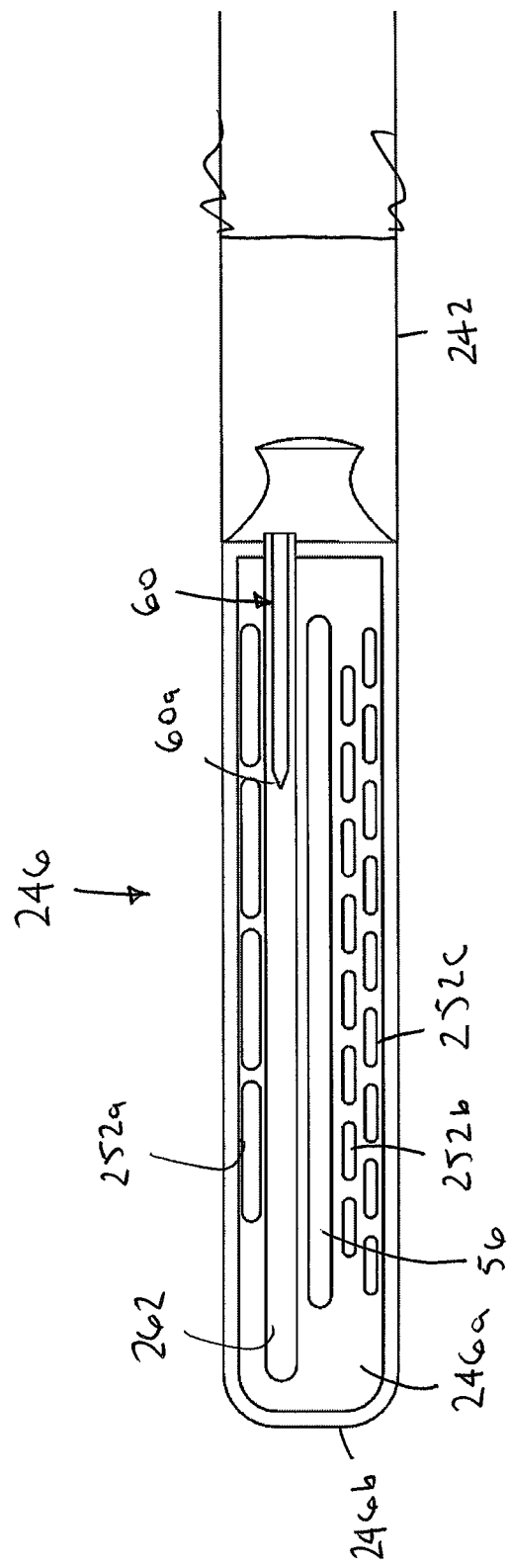

Alternatively, as shown in FIG. 4C, different size staples may be provided in one or more of the rows on the first jaw 246. For example, as shown, the first row may include receptacles 252a that are larger than the second and third rows of receptacles 252b, 252c. Consequently, larger staples may be deployed from the first row of receptacles 252a than the others. For example, it may be desirable to use larger staples to staple an appendix while smaller staples may be used to staple the blood vessel delivering blood to the appendix. Many smaller staples may enhance cutting off blood flow to the vessel, which may reduce risk of subsequent bleeding when the appendix is severed and removed. Thus, cartridges may be provided with multiple rows on either the left or right side of the cutting element 60 and with larger staples on the other side such that an appropriate cartridge may be selected and connected to the handpiece 30 based on the actual anatomy encountered. Optionally, one or more additional rows or sets of staples may be provided adjacent the first, second, and/or third rows. For example, multiple sets of staples (e.g., 1-5) may be delivered into the appendix being removed and/or into the intestine.

Returning to FIG. 3A, the contact surface 48a of the second jaw 48 may include corresponding recesses 54, e.g., arranged in rows opposite the receptacles 52, e.g., such that the recesses 54 are disposed directly above respective receptacles 52 in the closed position, e.g., to deform and/or otherwise close staples deployed from the receptacles 52, as described further elsewhere herein. For example, the recesses 54 may include ramped surfaces, anvils, and/or other features to deform one or both of the tines of the staples as they are deployed, as described further elsewhere herein.

Optionally, the second jaw 48 may include a Doppler radar or other sensor 58, e.g., located on the second contact surface 48a generally opposite the thermal element 56. For example, the Doppler sensor 58 may be an elongate crystal element mounted on the second contact surface 56 and aligned along the axis 26 (when the second jaw 48 is closed). The Doppler sensor 58 may be configured to transmit radar signals and receive reflections from the tissue captured between the jaws 46, 48 to identify whether blood is flowing within the tissue, e.g., using systems and methods known in the art.

As can be seen in FIG. 3C, the thermal element 56 and Doppler sensor 58 may be located opposite one another on the first and second jaws 46, 48, respectively, between the rows of staple receptacles 52 and recesses 54. This configuration may facilitate identifying blood flow within tissue captured between the jaws 46, 48 and then delivering thermal energy to cauterize, ablate, or necrose the tissue, e.g., to stop subsequent blood flow, as described elsewhere herein.

In an exemplary embodiment, the thermal element may include one or more electrodes, e.g., a single elongate electrode 56, e.g., extending axially along the first contact surface 46a, which may be coupled to a source of electrical energy, e.g., a generator (not shown), in the handle 30 and/or connected to the handle 30, as described further elsewhere herein. For example, as shown in FIG. 3C, the electrode 56 may include a thermal insulator block 56a, e.g., formed from ceramic and/or other material that is not electrically conductive, and an electrode element 56b supported by the block 56a, e.g., to prevent conduction from the electrode 56 to other components of the end effector 40 and/or delivering energy to tissue that is not directly contacted by the electrode element 56b. In the embodiment shown, a single electrode 56 may be provided for delivering radiofrequency energy in a mono-polar configuration to cauterize the contacted tissue, e.g., similar to Bovie® devices, as described elsewhere herein. Alternatively, multiple electrodes may be provided that are spaced apart from one another on the first contact surface 46a, which may be used to deliver RF energy in a bi-polar configuration. In a further alternative, other elements may be provided for delivering other forms of energy, e.g., laser, energy to cauterize contacted tissue.

Alternatively, the location of the thermal element 56 and Doppler sensor 58 may be reversed, if desired, e.g., with the thermal element on the second contact surface and the Doppler sensor on the first contact surface (not shown). In a further alternative, the thermal sensor may be omitted entirely and only a Doppler sensor 58 may be provided on one of the jaws, e.g., on the second jaw 48, as shown in FIG. 5A. Thus, in this alternative, the first jaw 46' does not include a thermal element.

In yet another alternative, the Doppler sensor may be provided at other locations on the second contact surface on any of these embodiments. For example, as shown in FIG. 5B, a Doppler sensor 58 may be provided along one side of the second jaw 48, i.e., adjacent the third row of recesses 54c opposite the third row of staple receptacles 52c.

In the embodiments shown in FIGS. 3C, 5A, and 5B, the Doppler sensor is oriented substantially perpendicular to the second contact surface. In this configuration, the centerline of the radar signals transmitted will also be perpendicular to the second contact surface. Alternatively, it may be desirable to orient the Doppler sensor at a non-perpendicular angle relative to the contact surface. For example, as shown in FIG. 5C, another example is shown in which a Doppler sensor 58''' is mounted on the second jaw 48''' such that the sensor defines an angle relative to the second contact surface 58a'''. Thus, in this alternative, the centerline of transmitted radar signals may directed diagonally from the second contact surface 58a'''. Such a configuration may be useful, e.g., to direct the radar signals towards a tissue structure of particular interest, e.g., towards the blood vessel of the appendix, e.g., defining an angle relative to the direction of blood flow rather than perpendicular to the direction of blood flow.

Returning to FIGS. 3A-3C, the end effector 40 may also include a blade or other cutting element 60 slidably disposed relative to the jaws 46, 48. For example, the first and second jaws 46, 48 may include respective slots or grooves 62, 64 aligned with the axis 26 that receive the blade 60, e.g., when the blade is advanced from a retracted position (not shown), e.g., received within the housing 42 immediately adjacent the contact surfaces 46a, 48a, to an advanced position, i.e., where a sharpened edge 60a of the blade 60 is advanced distally along the slots 62, 64 towards distal tips 46b, 48b of the jaws 46, 48 (the blade 60 is shown partially advanced in FIG. 3A). As can be seen in FIG. 3B, the blade 60 may extend between the contact surfaces 46a, 48a of the jaws 46, 48, such that the edge 60a cuts through or otherwise severs tissue (not shown) positioned between the jaws 46, 48 in the closed position, as described further elsewhere herein.

Optionally, the cartridge 40 may include one or more additional components for use during a procedure. For example, an illumination source and/or imaging element may be mounted on the housing 42, e.g., to facilitate imaging and/or monitoring use of the apparatus 8 during a procedure. In an exemplary embodiment, a CMOS, CCD, or other imaging element and/or one or more LEDs or other light sources (not shown) may be provided on the end effector 40, e.g., adjacent the proximal end of the first jaw 46 where the second jaw 48 pivots, that may be oriented distally to acquire images of the region beyond the stapler assembly 40. For example, the field of view of the imaging element may include the first contact surface 46a of the first jaw 46 such that an operator may use the images to position and/or orient a desired tissue structure on the contact surface 46a before actuating the second jaw 48 to close.

The apparatus 8 may be used to deliver staples into tissue during a medical procedure, e.g., during a laparoscopic surgical procedure, such as an appendectomy. Initially, a surgical space may be created, e.g., by introducing a trocar and/or cannula device (not shown) through the patient's skin and intervening tissue to a target region, e.g., the patient's abdominal cavity, and insufflating or otherwise opening the space to access a desired tissue structure, such as an appendix indicated for removal.

An end effector 40 and cartridge 50 may be selected and connected to the distal end 24 of the shaft 20 before introduction into the patient's body. For example, based on the anatomy encountered, the operator may select a cartridge 50 including a particular arrangement of staples, e.g., including uniform-size staples or different size staples, such as those described elsewhere herein, insert the cartridge 50 into the cavity 46c of the first jaw 46, e.g., before or after connecting the end effector 40 the shaft 20. Once the apparatus 8 is ready, the distal end 24 of the shaft 20 carrying the end effector 40 may be introduced into the surgical space, e.g., through a cannula or other port (not shown), until the jaws 46, 48 are located the surgical space. For example, the surgical space may be initially accessed using a needle, trocar, and/or dilator device, e.g., punctured through the patient's skin and intervening tissue into the abdominal cavity to approach the appendix, and a cannula may be positioned through the puncture. Gas may be delivered through the cannula or other device to insufflate and create a surgical cavity or space.

The distal end 24 of the shaft 40, carrying the selected end effector 40 and/or cartridge 50, may then be introduced through the cannula into the surgical space. For example, the jaws 46, 48 may be initially locked in the closed position to facilitate introduction through the cannula and then may be released once located within the surgical space, whereupon the second jaw 48 may open. Alternatively, the second jaw 48 may be biased to open but may be manually or otherwise closed to allow insertion through the cannula.

With the jaws 46, 48 in the open position within the surgical space, tissue within the region, e.g., the patient's appendix, may be placed on the contact surface 46a of the first jaw 46 and/or otherwise positioned between the jaws 46, 48. For example, both the appendix and the appendicular artery may be positioned between the jaws 46, 48, e.g., with one distal to the other depending on the orientation of the appendix.

Once the tissue is positioned as desired, the trigger actuator 34 may be manipulated to close the second jaw 48 and lock the tissue in place between the contact surfaces 46a, 48a. For example, the trigger 34 may include a ratchet mechanism that allows the second jaw 48 to close while preventing it from reopening, or a separate locking mechanism (not shown) may activated once the second jaw 48 is closed to engage the tissue. A separate staple actuator (not shown) may then be used to deploy one or more staples from the first jaw 46 into and through the tissue and towards the second jaw 48 to deform the staples(s) and engage the tissue.

Figure 15C:
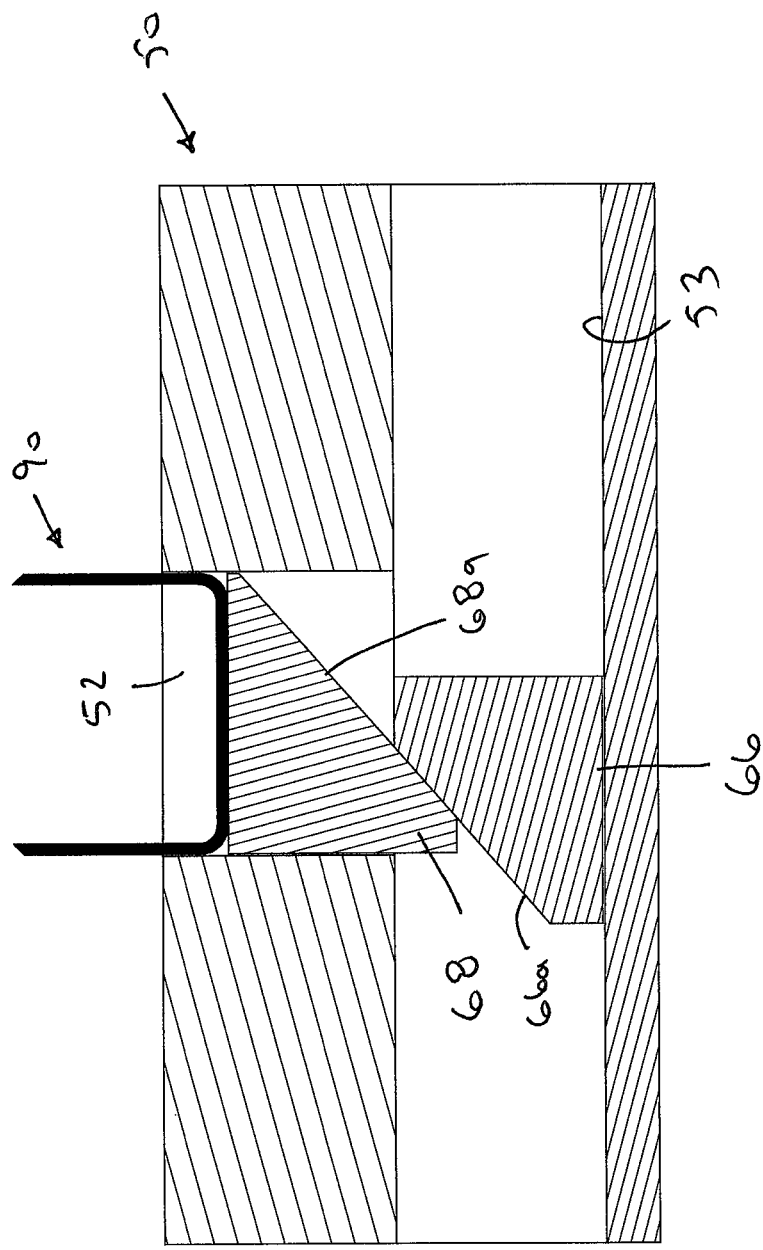
Figure 15D:
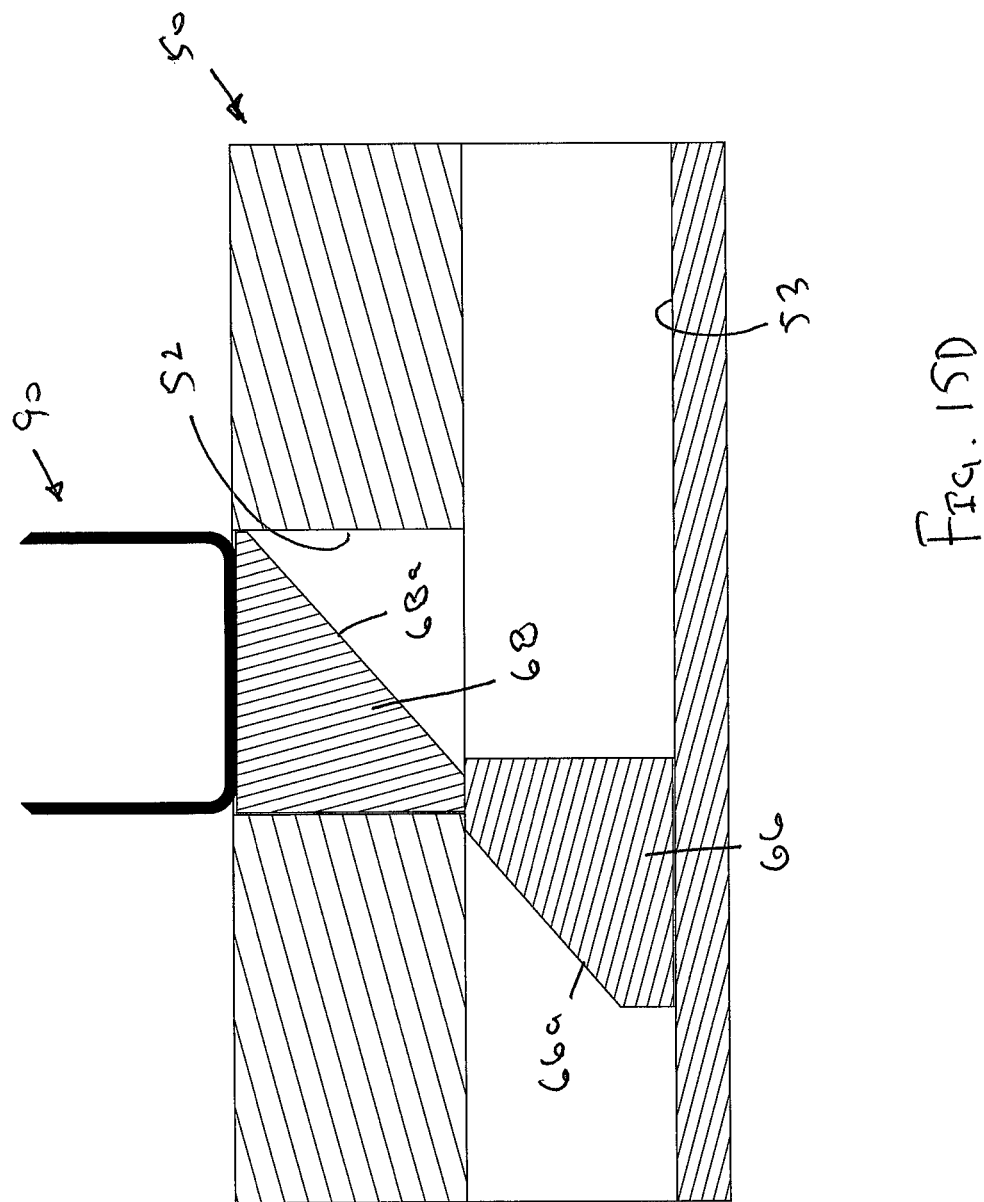
Figure 17:
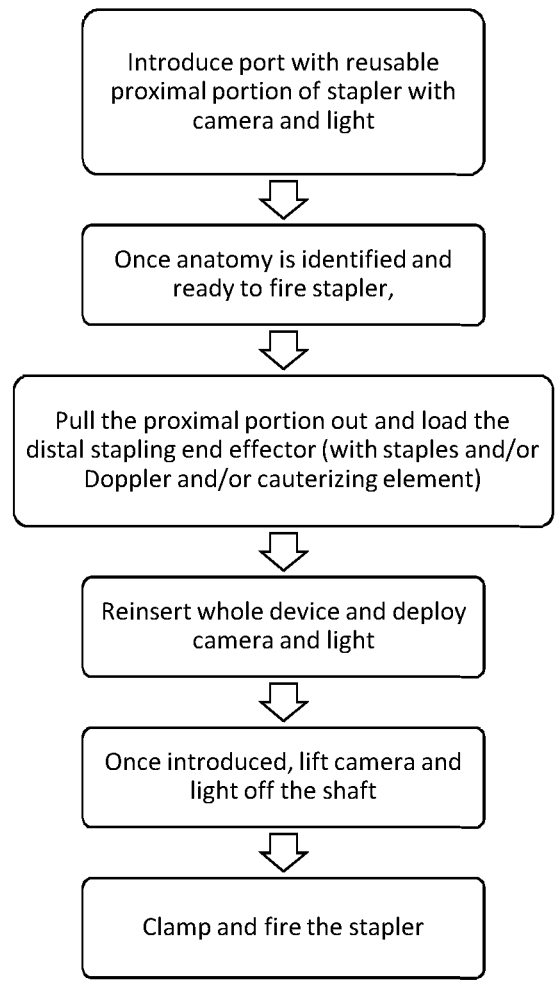
FIG. 17 is a flowchart showing an exemplary method for using an access port and stapler to perform a surgical procedure.

For example, as the stapler actuator is pushed, an actuation shaft (not shown) within the shaft 20 may advance a wedge or other staple actuation element (not shown) within the cartridge 50 or end effector 40 to begin deploying staples from the receptacles 52 out of the first contact surface 50a/46a of the first jaw 46 upwardly towards the second jaw 48, thereby causing one or more tines of the staples to contact the corresponding recesses 54 in the second contact surface 48a and deform to staple the tissue. FIGS. 15A-15D show an exemplary embodiment of a wedge actuator 66 slidable within a passage 53 within a cartridge 50 that includes an angled or ramped distal surface 66a that may push corresponding ramped surfaces 68a of pistons (one piston 68 shown) within respective receptacles 52 upwardly to push the corresponding staples 90 towards the second jaw 48 (not shown in FIGS. 15A-15D), where tines of the staples 90 are deformed within the corresponding recesses 54, as described elsewhere herein. For example, the wedge 66 may be coupled to a stapler actuator shaft (not shown) that may be advanced and retracted within the passage 53, e.g., to advance the wedge 66, thereby slidably engaging the ramped surface 66a of the wedge 66 with ramped surfaces 68a of the pistons 68 and directing the pistons 68 upwardly in the respective receptacles 52, as shown in FIGS. 15B-15D. The wedge 66 may then be retracted back to the position shown in FIG. 15A. It will be appreciated that other stapler mechanisms may be used instead, such as those disclosed in U.S. Pat. Nos. 4,608,981, 4,633,874, 5,104,025, 5,307,976, 5,709,680, and European Patent No. 1,157,666, the entire disclosures of which are expressly incorporated by reference herein.

The deployment of the staples may be sequential within each set, e.g., simultaneously delivering first staples from each of the sets 52a-52c at the proximal end of the first jaw 46 and, as the trigger 34 continues to be pulled, additional staples are deployed until the desired length of stapling, whereupon actuation may be discontinued, which may leave one or more staples closest to the distal tip 46a of the first jaw 46 undeployed. In this manner, the operator may control how many staples are deployed based on the extent to which the staple actuator is pulled. Alternatively, the actuator 34 may be binary, i.e., wherein, when the trigger 34 is initially pulled, all of the staples in the first jaw are deployed in rapid succession.

If the apparatus 8 includes a Doppler sensor 58, e.g., on the second jaw 48, the Doppler sensor 58 may be activated, e.g., using a radar actuator (not shown) on the handle 30, to detect blood flow in the stapled tissue. For example, signals from the sensor 58 may be transmitted, e.g., via one or more wires (not shown) in the shaft 20 to a processor in the handle 30, which may analyze the signals to confirm whether blood flow has discontinued in the stapled tissue. The apparatus 8 may include an output device, e.g., an indicator light, speaker, and the like (not shown), e.g., on the handle 30 that may provide a positive indication that blood flow has stopped. The operator may then manipulate another actuator, e.g., a slider, dial, and the like (not shown) on the handle 30 to advance the blade 60 to sever the stapled tissue from adjacent tissue.

If the output device indicates that blood is still flowing in the stapled tissue, additional actions may be taken to cauterize the tissue and/or stop blood flow. For example, if the apparatus 8 includes the thermal element 56, the operator may activate the thermal element to deliver thermal energy to the stapled tissue. For example, a button or switch (not shown) on the handle 30 may be activated to deliver RF energy from a power source coupled to the handle 30 via one or more wires (not shown) in the shaft 20 to the electrode(s) 56a on the first jaw 46 to cauterize the stapled tissue. Energy may be delivered until the output device/Doppler sensor 58 provides a confirmation that blood flow has stopped, whereupon the blade 60 may be advanced to sever the tissue, e.g., to simultaneously sever the appendix and the appendicular artery.

Optionally, before severing the tissue, the second jaw 48 may be released and opened and the jaws 46, 48 repositioned relative to the stapled tissue and then closed and locked at one or more subsequent positions, e.g., to use the Doppler sensor 58 to confirm blood flow has stopped and/or deliver further thermal energy to cauterize the tissue. Once desired, the blade 60 may be used to sever the tissue.

The apparatus 8 may then be removed from the surgical space and the procedure completed using conventional methods. For example, the blade 60 may be retracted, and the Doppler sensor 58 and/or hemostasis element 56 may be deactivated (if not already). The end effector 40 may be removed from the patient's body with the second jaw 48 remaining locked to remove the excised tissue.

Optionally, the procedure may be illuminated and/or monitored using an illumination source and/or imaging element on the end effector 40 and/or shaft 20, as described elsewhere herein. In addition or alternatively, other light sources and/or imaging devices may be provided to monitor the procedure. For example, a separate endoscope may be introduced into the surgical space, e.g., via a different cannula or port (not shown) than the cannula used to introduce the apparatus 8.

In another alternative, a cannula or access port may be provided that includes one or more illumination and/or imaging elements, and the apparatus 8 may be introduced using the access port. For example, turning to FIGS. 6A-6E, an exemplary embodiment of an access port 70 is shown that generally includes an elongate tubular body 72 including a proximal end 74, a distal end 76 sized for introduction into a patient's body, and one or more lumens or passages 78 extending at least partially between the proximal and distal ends 74, 76. For example, the tubular body 72 may include a primary lumen 78a sized to receive one or more instruments therethrough that extends from an outlet in the proximal end 74 to an outlet in the distal end 76, such as any of the stapler apparatus described elsewhere herein. In addition, the tubular body 72 may include one or more secondary lumens (not shown), e.g., extending at least partially from thee proximal end 74 towards the distal 76, e.g., for receiving actuator elements, wires, and/or other components, as described elsewhere herein. The tubular body 72 may be substantially rigid or alternatively at least a portion of the tubular body 72, e.g., a distal portion, may be malleable or flexible (not shown).

A handle or hub 80 may be provided on the proximal end 74, e.g., to facilitate manipulation of the access port 70 during use. The hub 80 may include one or more valves or seals (not shown), which may seal the primary lumen 78a yet facilitate inserting an instrument into the primary lumen 78a, e.g., providing a substantially fluid-tight seal around the instrument. In this manner, the seal(s) may prevent insufflation gas or other fluid to escape through the primary lumen 78a, e.g., when the access port is introduced into a patient's body, as described elsewhere herein.

In addition, a display or other output device 82 may be provided on the hub 80, e.g., to facilitate observing or otherwise monitoring the procedure using one or more imaging devices on the access port 80. For example, a distal portion of the tubular body 72 may include a pair of deployable arms 84 including first ends 84a pivotally coupled to the tubular body 72 and second or free ends 84b that may carry one or more cameras, light sources, and/or other imaging device, as described further below.

In one embodiment, the display 82 may be removably mountable on the hub 80, which may include one or more connectors or cables (not shown) that may be coupled to corresponding connectors on the hub 80, which are, in turn, coupled to one or more wires extending to the imaging device(s) on the arms 84. Thus, in this alternative, the display 82 may be reusable and the tubular body 72 may be disposable/single-use. Alternatively, the display 82 may be permanently mounted to the hub 80 and one or more wires or other elements may communicate with the imaging device(s). Thus, in this alternative, the entire access port 80 may cleaned and reused or may be single-use. In a further alternative, the access port 80 may include a communications interface that may transmit signals from the imaging device wirelessly, e.g., using Bluetooth or other communications protocols, to allow images to be presented on a remote display.

In an exemplary embodiment, a CMOS, CCD, or other imaging element (not shown) may be provided on the free end 84b of one of the arms 84 and one or more LEDs or other light sources may be provided on the free end 84b of the other arm 84. Alternatively, separate light sources and imaging elements may be provided on both arms, e.g., to provide multiple images simultaneously on the display 82. In a further alternative, only one arm may be provided, if desired, including one or more light sources and/or imaging elements on its free end.

In any of these embodiments, one or more wires may transmit signals from the imaging element(s) to the display 82, which may include a processor to process the signals and present the images on a screen of the display 82. The imaging element(s) may include a field of view oriented distally beyond the distal end 76 of the tubular body 72, e.g., to illuminate and/or image an instrument deployed within a region beyond the distal end 76.

Figure 6B:
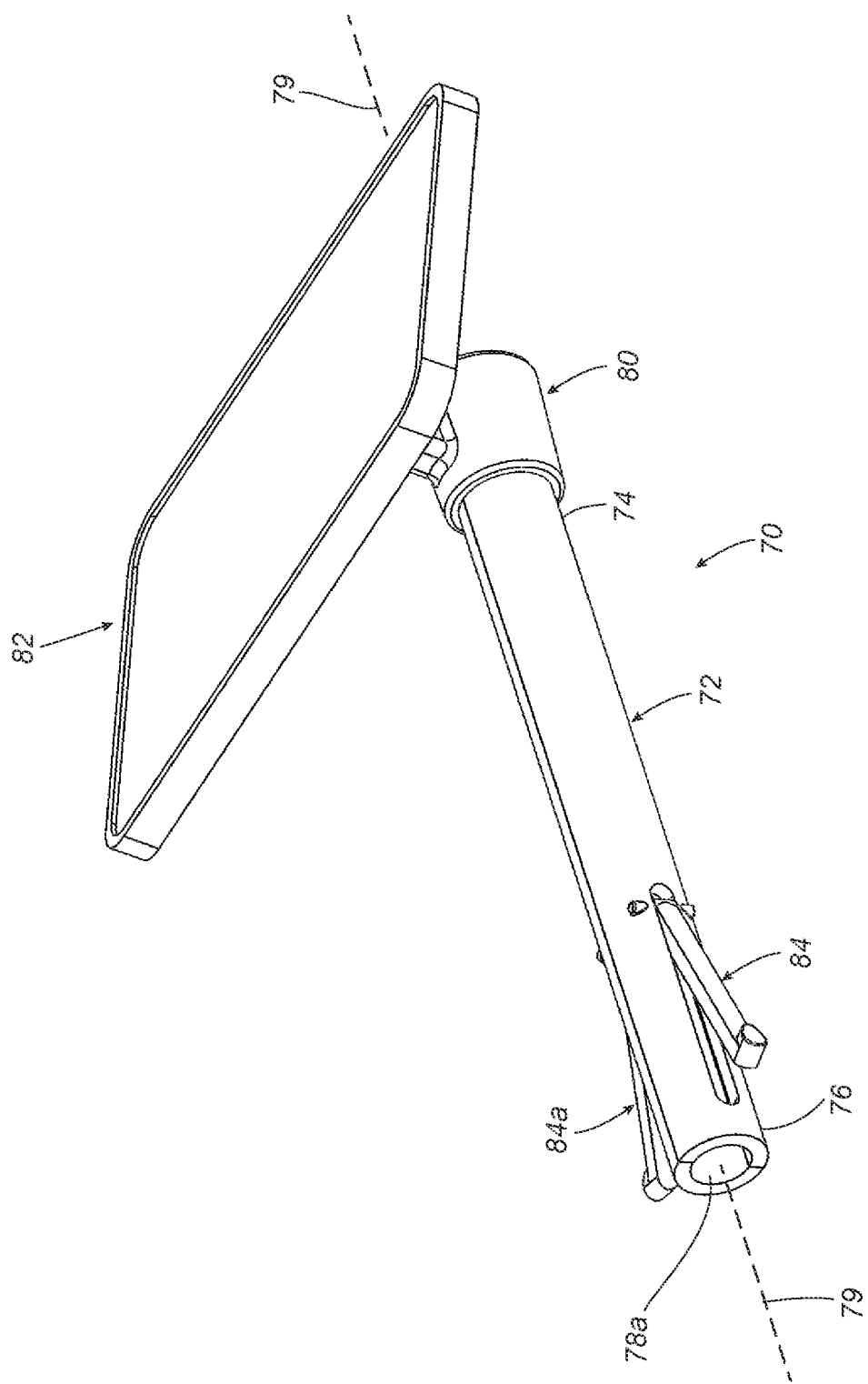
Figure 6C:
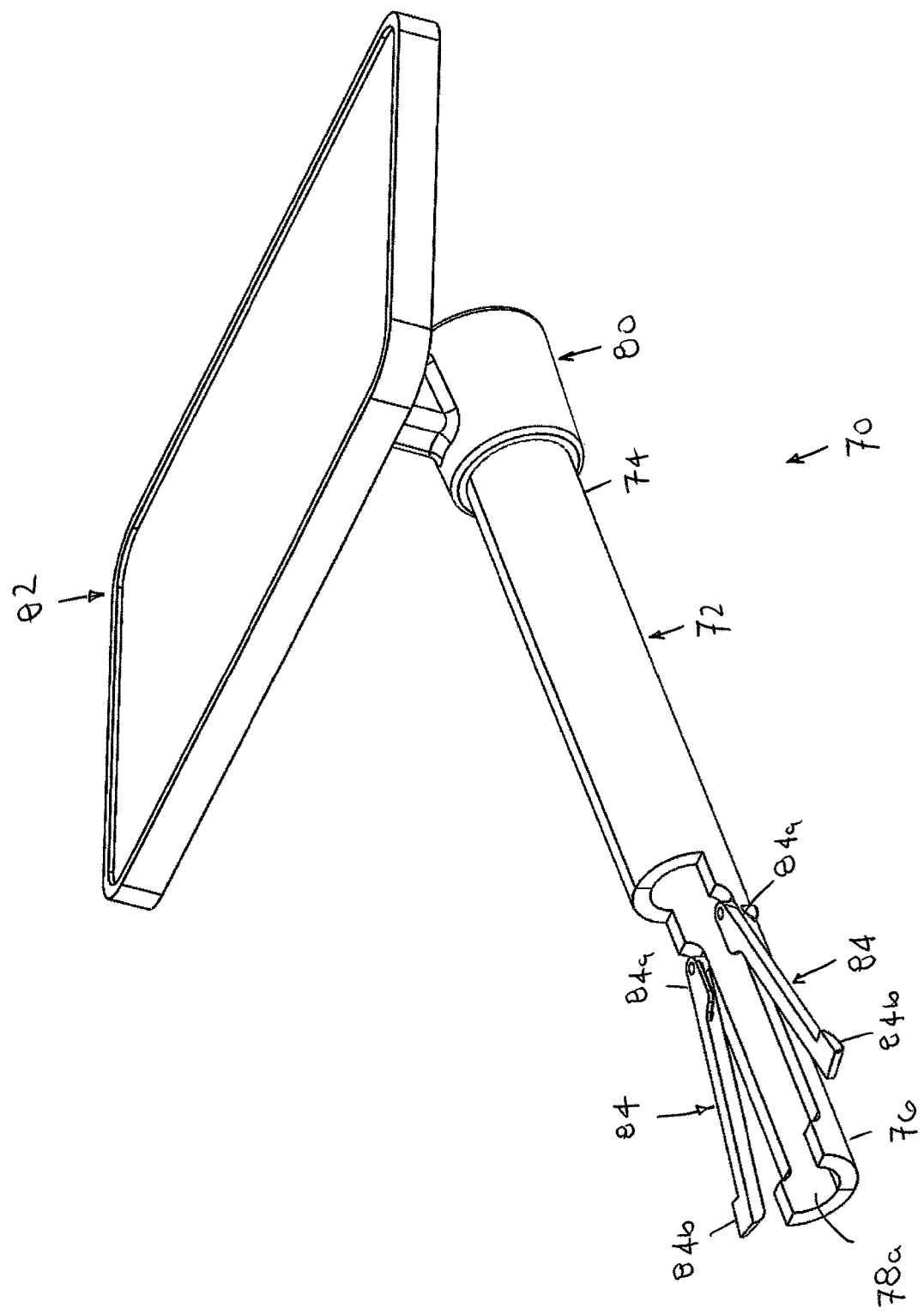
FIG. 6C is a perspective view of the access port of FIGS. 6A and 6B with a portion of the tubular shaft removed to show details of the deployment arms of the imaging system.
Figure 6D:
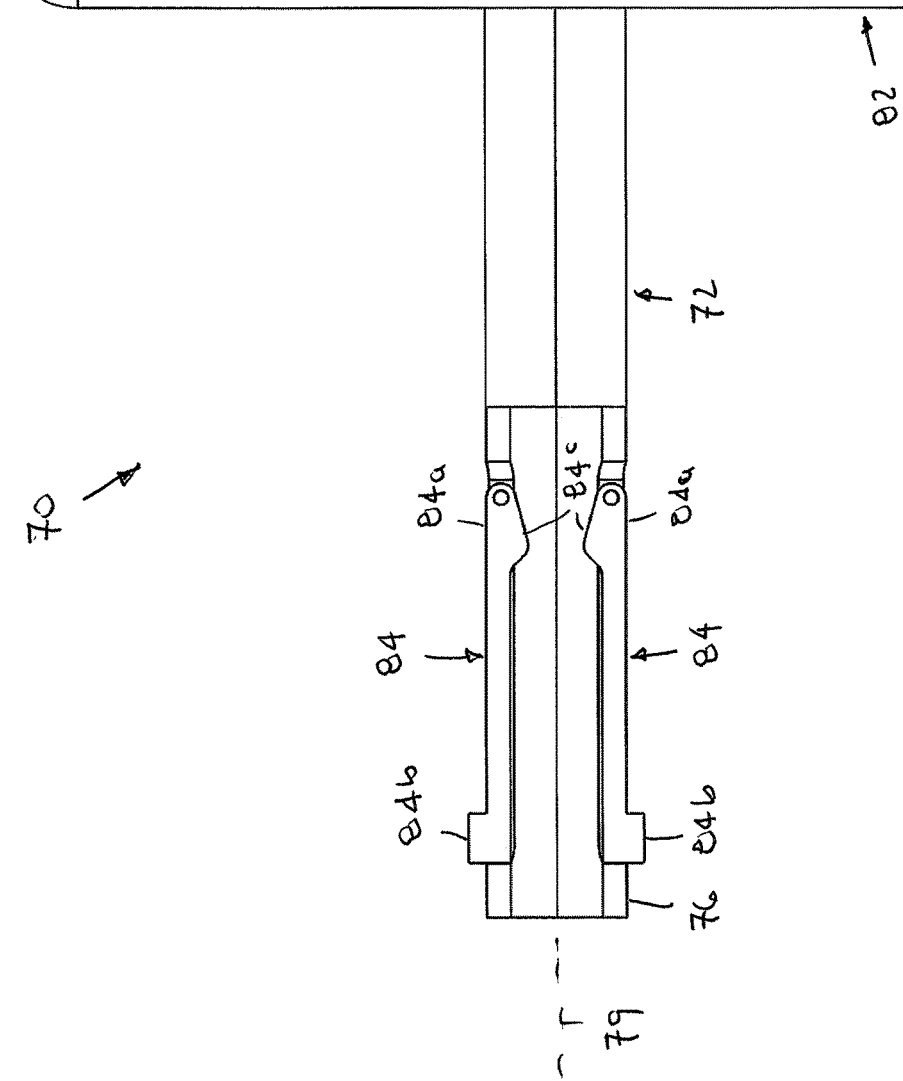

The arms 84 are movable between a retracted configuration, e.g., as shown in FIGS. 6A and 6D, which may facilitate introduction into a patient's body, and a deployed configuration, e.g., as shown in FIGS. 6B, 6C, and 6E, where the imaging device may be used to acquire images during a procedure. In one embodiment, the arms 84 may be biased to the retracted configuration, but may be directed to the deployed configuration when an instrument is inserted into the primary lumen 78a, as described further below. Alternatively, the arms 84 may be actuated (or moved) by a user selectively between the retracted and deployed configurations, if desired.

For example, with particular reference to FIGS. 6D and 6E, the first ends 84a of the arms 84 may include ramps or other features 84c that extend partially into the primary lumen 78a. Consequently, when an instrument is inserted into the lumen 78a, the instrument may contact the ramps 84c, thereby deflecting the arms 84 outwardly to the deployed configuration. As can be seen in FIG. 6E, in the deployed configuration, the ramps 84c may be substantially flush with the wall of the tubular body 72 such that the ramps 84c do not interfere with manipulation of the instrument. When the instrument is removed, the arms 84 may return automatically back towards the retracted configuration. Alternatively, the arms 84 may remain deployed until actuated or until the access port 70 is removed, e.g., whereupon the arms may be collapsed inwardly as they contact tissue along the exit path. In another alternative, a circumferential light source, such as a circular Xenon LED lamp (not shown) may be provided on the distal end of the access port instead of the arms.

Figure 7A:
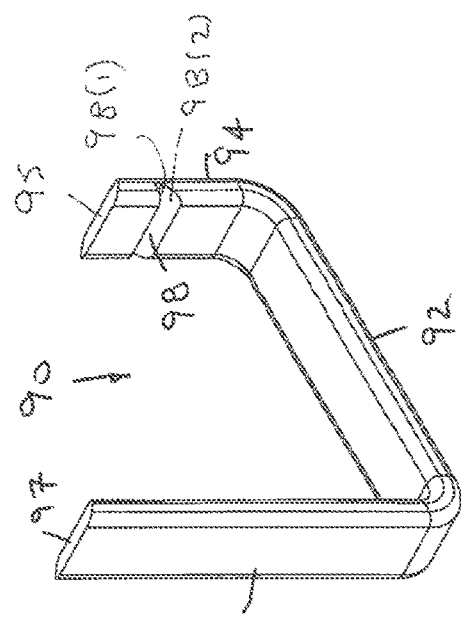
FIGS. 7A and 7B are perspective views of an exemplary embodiment of a staple or clip that may be delivered using the stapler apparatus herein.
Figure 7B:
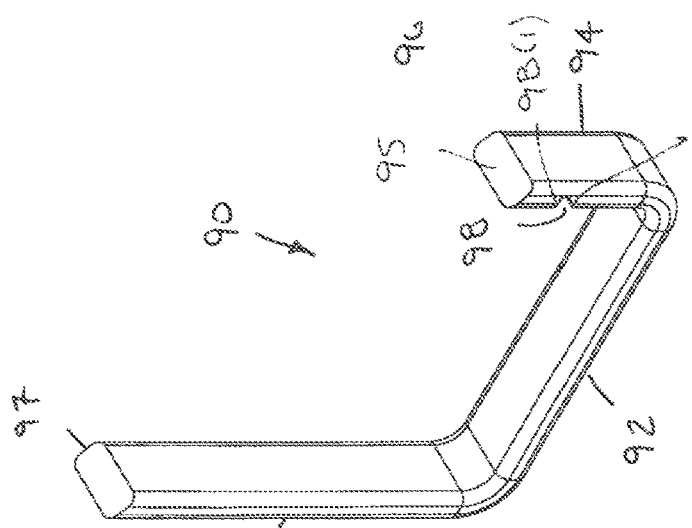
Figure 7D:
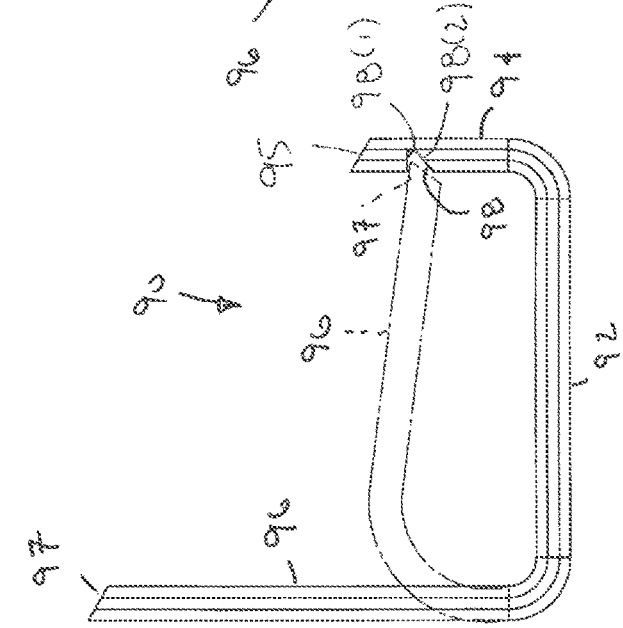
FIG. 7D is a side view of the staple of FIGS. 7A and 7B, showing a first tine of the staple being deformed and engaged with a second tine of the staple.

Turning to FIGS. 7A-7D, an exemplary embodiment of a staple or clip 90 is shown that may be delivered using any of the stapler apparatus herein. Generally, the staple 90 includes a base 92, e.g., a substantially straight segment, from which first and second tines 94, 96 extend, e.g., substantially perpendicular to the base 92. The tines 94, 96 may be substantially straight terminating in respective tips 95, 97. Thus, for example, the base 92 and tines 94, 96 may define a substantially rectangular "U" shape, e.g., with rounded transitions between the base 92 and the tines 94, 96. As shown, the first tine 94 has a length that is substantially shorter than the second tine 96. In addition, the second tine 96 has a length from the base 92 to its tip 97 that is longer than the length of the base 92. Consequently, the second tine 96 may be bent or otherwise deformed towards the first tine 94, e.g., as shown in FIG. 7D.

In the example shown, the staple 90 has a cross section that is substantially uniform along the length of the staple 90, e.g., along a length of the first tine 94, along the base 92, and along the second tine 96. For example, the staple may have a substantially rectangular (with or without sharp corners), oblong, or other generally flattened cross-section, e.g., having a width "w" that is thicker than a thickness "t," as indicted in FIGS. 7A-7D.

In addition, the first tine 94 includes a notch 98 adjacent its tip 95 configured to receive the tip 97 of the second tine 96 when it is deformed. As shown, the notch includes a blunt upper edge 98(1) and a tapered lower edge 98(2). For example, as shown, the tip 97 of the second tine 97 may be beveled such that the tip 97 tapers towards the first tine 94, which may enhance the tip 97 being locked into the notch 98. Alternatively, as shown in FIG. 8A, the tip 97a of the second tine 96a may be beveled in the opposite direction, i.e., away from the first tine 92a. In addition, or alternatively, the staple may include different ridges for different thickness compression.

Optionally, as shown in FIG. 8C, the first tine 94c may include a plurality of notches 98c spaced apart from one another along the length of the first tine 94c. Thus, in this embodiment, the tip 97c of the second tine 96c may be ratcheted sequentially into the notches 98c, e.g., simply locked into the top notch 98c or down into one of the notches further down on the first tine 94c. Although three notches 98c are shown in FIG. 8C, it will be appreciated that any desired number of notches (two or more) may be provided on the first tine 94c. Alternatively, the first tine may be provided without any notches (not shown), and the stapler actuator may be configured to bend or otherwise deform the tip of the first tine over the second tine (after the second tine has been bent).

In another option, shown in FIG. 8B, a radius of the transition between the base 92b and the second tine 96b may be increased, e.g., compared to the staple 90 shown in FIG. 7C, which may reduce the force to bend the second tine 96b during use. In yet another option, shown in FIG. 8D, the tip 95d of the first tine 94d may include a bevel that is oriented towards the second tine 96d (as opposed to being oriented away from the second tine 96, as in the staple 90 shown in FIG. 7C). In still another option, shown in FIG. 8E, a staple 90e may be provided that includes a bump 93e in the base 92e, which may be configured to enhance the pinching/closure of the tissues entrapped within the staples. It will be appreciated that any of these options may be included in one or more of the staples included in any of the stapler apparatus described elsewhere herein.

With additional reference to FIGS. 3A-3C, a plurality of staples, such as staple 90 shown in FIGS. 7A-7D (or any of the alternatives) may be provided in each of the receptacles 52 in the first jaw 46. With the receptacles 52 aligned along the axis 26 of the shaft 20, the base 92 of each staple 90 may be seated at the bottom of the respective receptacle with the first tine 94 closer to the distal tip 46b of the first jaw 46 and the second tine 96 closer to the proximal housing 42 (or reverse). Consequently, as the staples are deployed upwardly from the receptacles 52, both tines 94, 96 may be driven through the tissue adjacent the contact surface 46a of the first jaw 46, and the second tines 96 may then be received in the respective recesses 54 in the second jaw 48 as the staples are pushed upward toward the second jaw 48. This action may facilitate bending the second tines 96 distally towards the first tines 94. Thus, the second tines 96 may be bent or otherwise deformed above the tissue towards the tips 93 of the first tines 94 until the tips 97 of the second tines 96 are received in the respective notches 98, thereby locking the staples 90 and compressing the captured tissue.

Figure 18A:
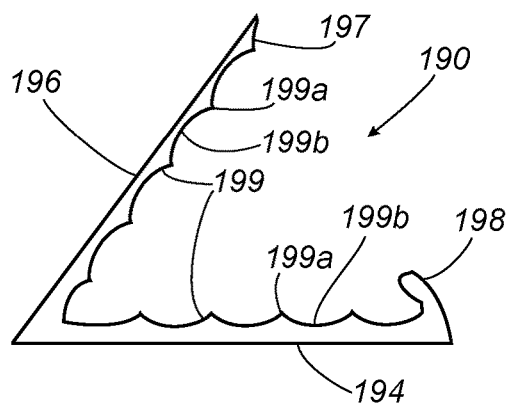
FIGS. 18A and 18B show another example of a staple including opposing arms in open and closed configurations, respectively.
Figure 18B:
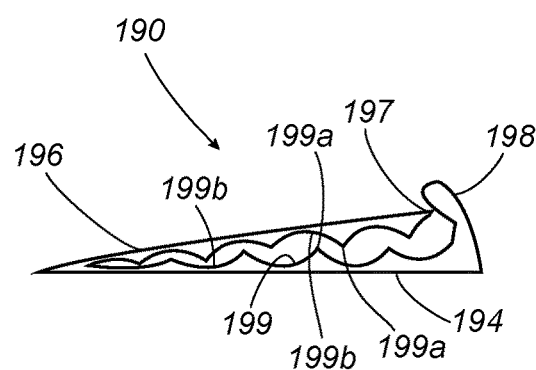
Figure 19:
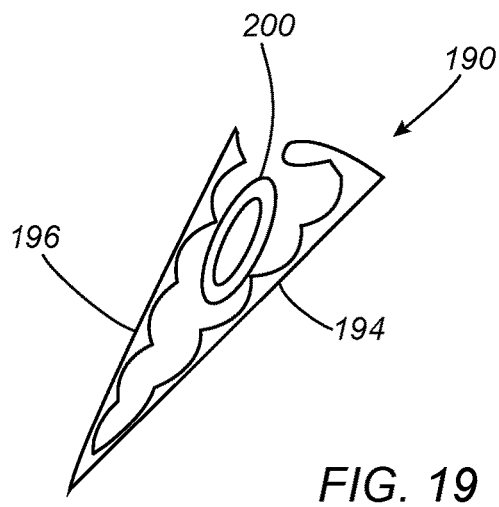
FIG. 19 shows the staple of FIGS. 18A and 18B in the closed configuration, capturing a vessel between the opposing arms.

FIGS. 18A and 18B show another example of a staple 190 that may be used in the staplers herein, e.g., to staple a blood vessel 200, e.g., as shown in FIG. 19. As shown, the staple 190 has a V-shape including a first arm 194 and a second arm 196, each with serrated edges 199 including multiple notches on their opposing edges, i.e., including alternating teeth 199a spaced apart by troughs 199b on each serrated edge 199. As shown, the first arm 194 includes a catch 198 and the second arm 196 may be directed from the open position where the second arm 196 is spaced apart from the first arm 194, e.g., as shown in FIG. 18A, towards the first arm 194 such that a tip 197 of the second arm 196 is captured under the catch 198, e.g., as shown in FIG. 18B. As can be seen in FIG. 18B, when the staple 190 is closed, the serrated edges 199 may be out of alignment such that they cross one another to enhance closing a lumen for better bleeding control, e.g., as shown by the blood vessel 200 captured between the arms 194, 196 in FIG. 19. For example, as shown in FIG. 18B, the teeth 199a of one serrated edge 199 are offset from the teeth 199a of the opposite serrated edge 199 such that the teeth 199a are disposed aligned with troughs 199b of the opposite serrated edge 199 when the staple 190 is closed.

Figure 9A:
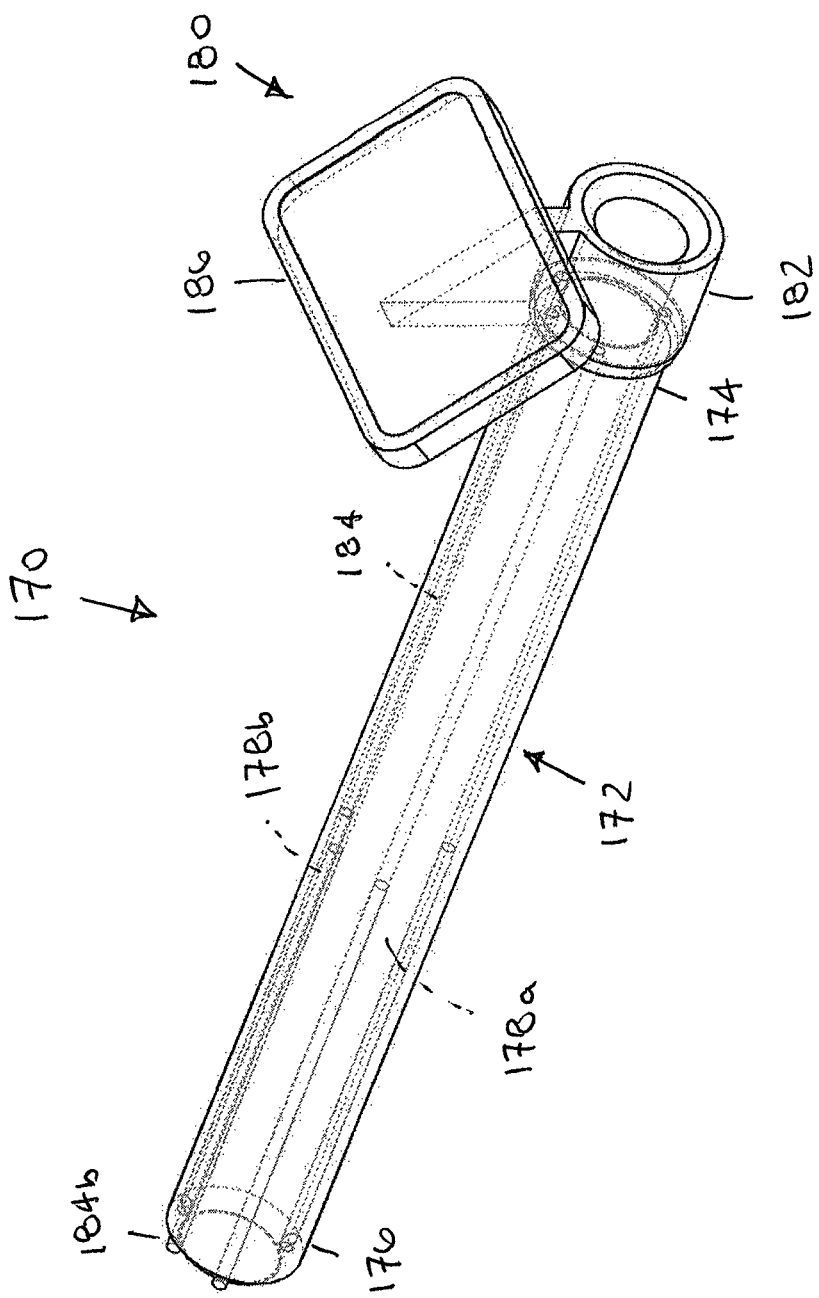
FIGS. 9A and 9B are perspective and side views, respectively, of another exemplary embodiment of an access port including a disposable tubular member and a reusable video module that may be coupled to the tubular member.
Figure 9B:
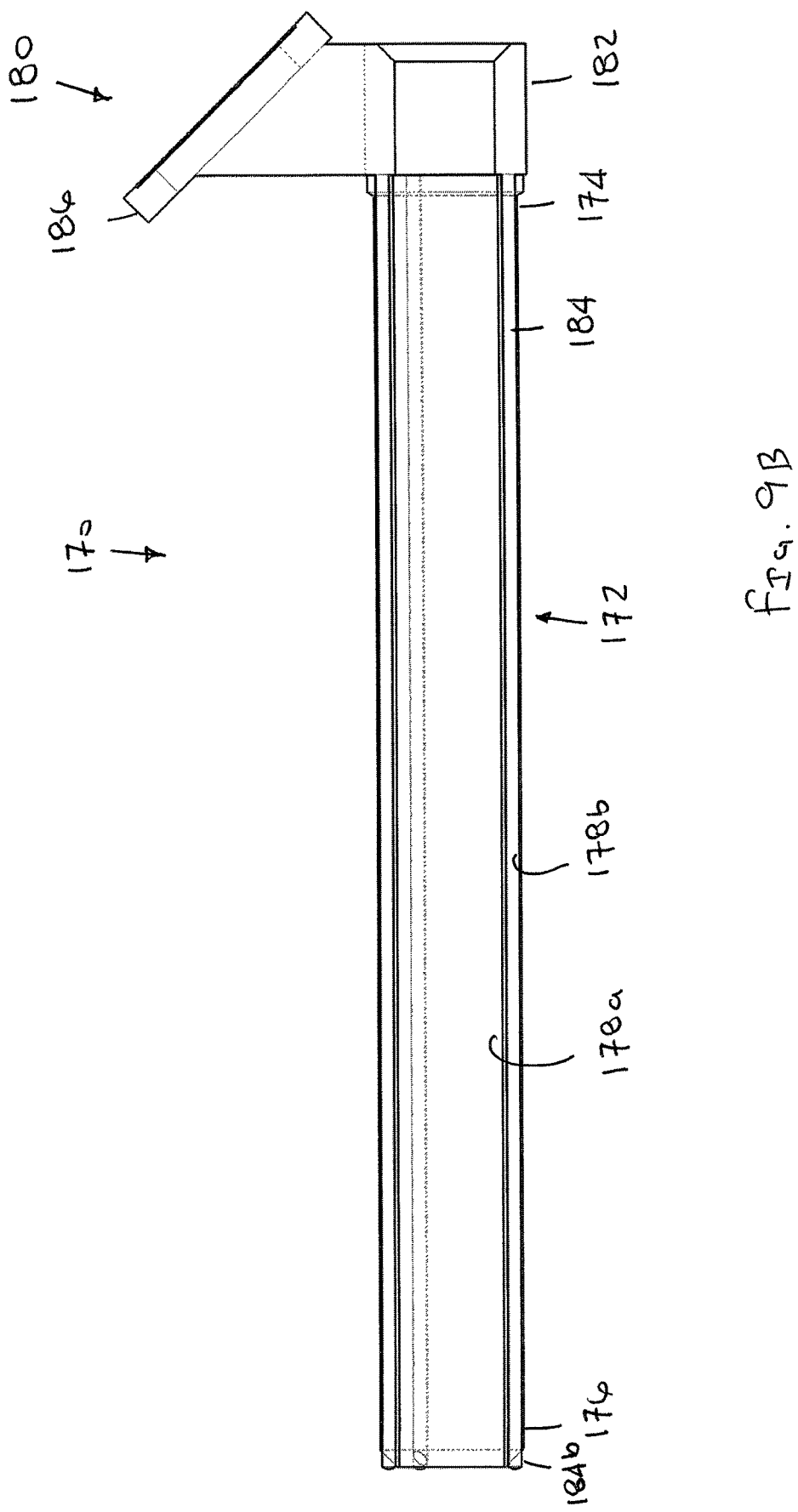
Figure 9C:
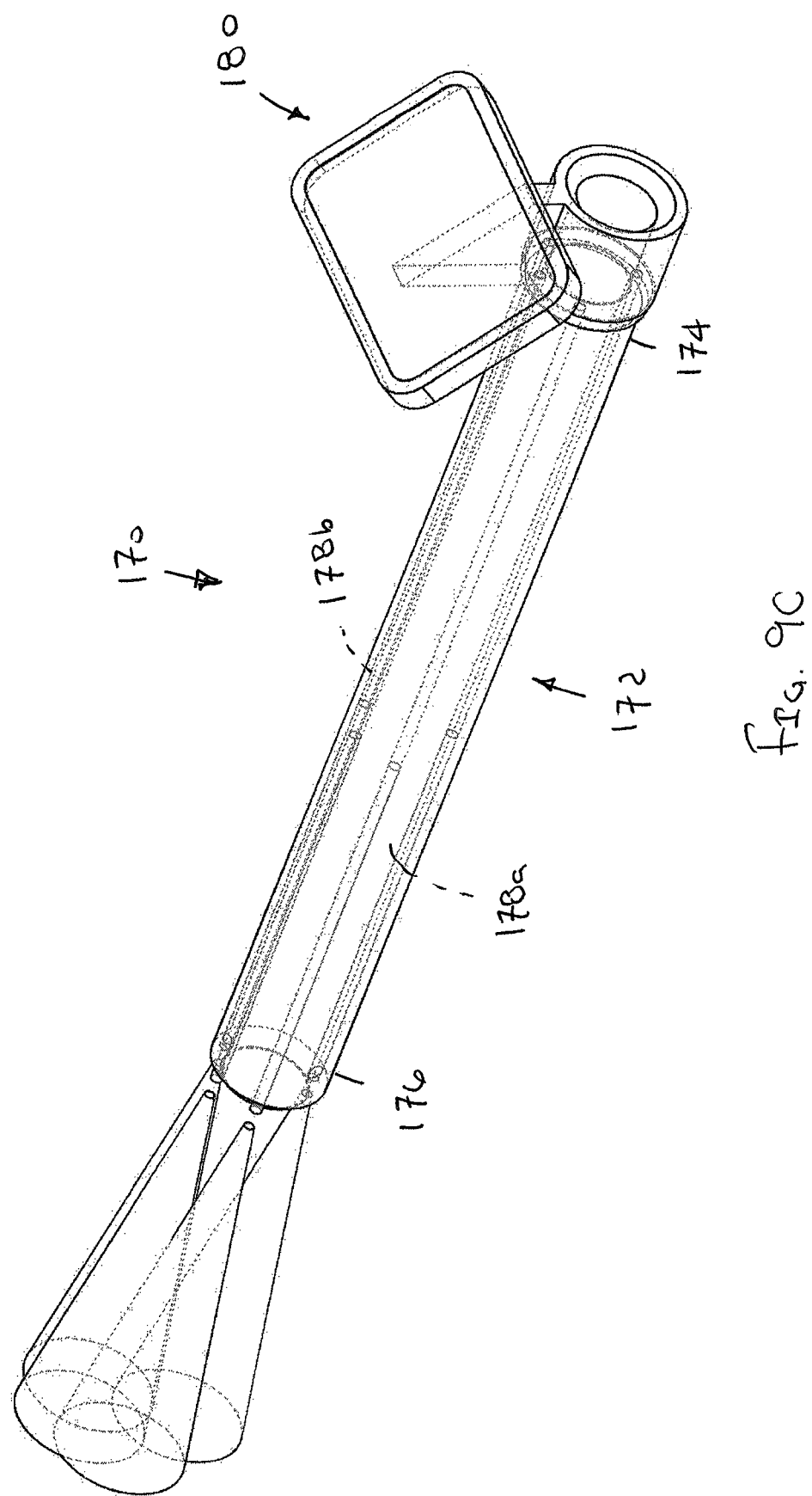
FIG. 9C is a perspective view of the access port of FIGS. 9A and 9B with imaging elements of the video module activated.
Figure 10:
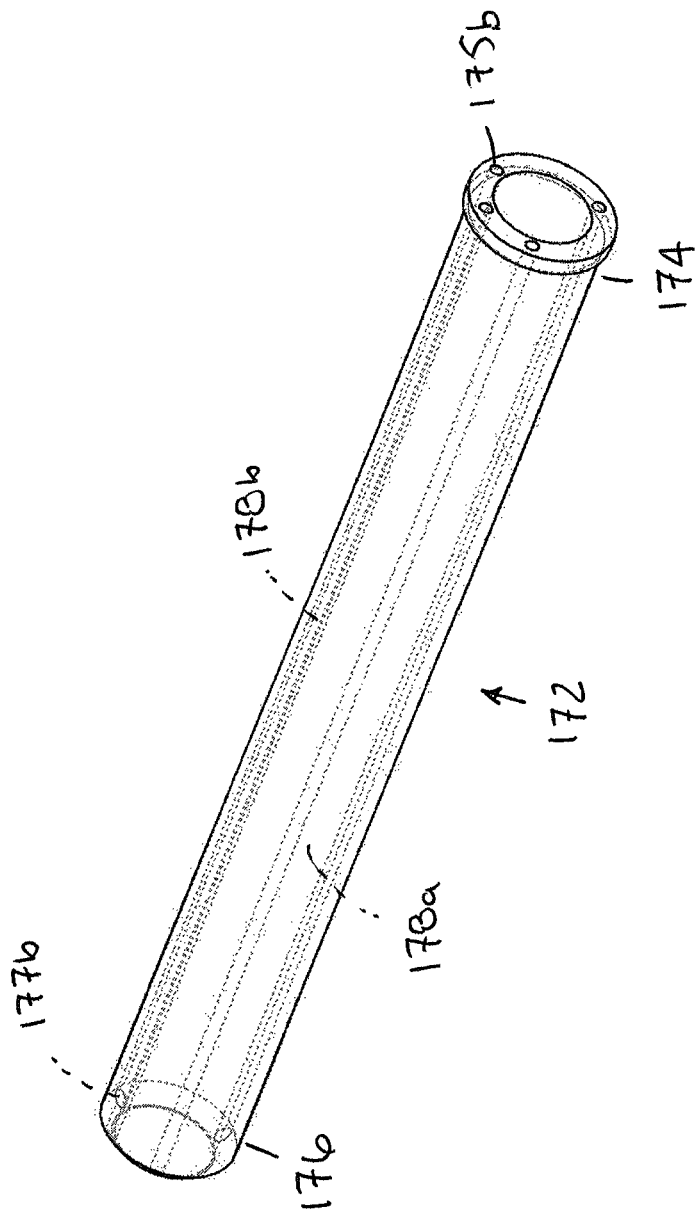
FIG. 10 is a perspective view of the tubular member of FIGS. 9A-9C.

Turning to FIGS. 9-12, another exemplary embodiment of an access port 170 is shown that includes an elongate tubular body 172 and a video module 180 that may be coupled to the tubular body 172, e.g., to allow introduction of one or more instruments through the port 170 into a surgical space within a patient's body while acquiring images within the surgical space, generally similar to other embodiments herein. As shown in FIG. 10, the tubular body 172 includes a proximal end 174, a distal end 176 sized for introduction into a patient's body, and one or more lumens or passages 178 extending between the proximal and distal ends 174, 176. For example, the tubular body 172 may include a primary lumen 178a sized to receive one or more instruments therethrough, such as the stapler apparatus 8 shown in FIGS. 13A and 13B and/or described elsewhere herein. In addition, the tubular body 172 includes one or more secondary lumens 178b, e.g., positioned within a sidewall of the tubular body 172 around the primary lumen 178a. For example, as best seen in FIGS. 12A and 12B, three secondary lumens 178b may be positioned together on one side of the primary lumen 178a and a fourth secondary lumen 178b may be provided on an opposite side of the primary lumen 178a to acquire two sets of images simultaneously, as described further elsewhere herein. Outlets 179b of the secondary lumens 178b at the distal end 176 may be open or may include a transparent cover, membrane, and the like (not shown) to prevent bodily fluids or other materials from entering the secondary lumens 178b from the distal end 176. The tubular body 172 may be substantially rigid or alternatively at least a portion of the tubular body 172, e.g., a distal portion, may be malleable or flexible (not shown).

The video module 180 generally includes an annular hub 182 from which a plurality of elongate sleeves, tubes, or other imaging elements 184 extend, e.g., provided in an arrangement corresponding to the secondary lumens 178b in the tubular body 172. The imaging sleeves 184 may be sized to be inserted into the secondary lumens 178b simultaneously from the proximal end 174 of the tubular body 172 such that distal tips 184b thereof are disposed adjacent the distal end 176 of the tubular body 172, e.g., extending slightly from the outlets 184b for acquiring images beyond the distal end 176.

Optionally, the proximal end 174 of the tubular body 172 and the hub 182 may include cooperating connectors (not shown) to removably couple the hub 182 to the tubular body 172, e.g., such that the access port 170 may be manipulated as a unitary device.

In addition, one or both of the proximal end 174 of the tubular body 172 and the hub 182 may include one or more valves or seals (not shown), e.g., to seal the primary lumen 178a yet facilitate inserting an instrument into the primary lumen 178a, e.g., providing a substantially fluid-tight seal around the instrument. In this manner, the seal(s) may prevent insufflation gas or other fluid to escape through the primary lumen 178a, e.g., when the access port 170 is introduced into a patient's body, as described elsewhere herein.

In addition, a display or other output device 186 may be provided on the hub 182, e.g., to facilitate observing or otherwise monitoring the procedure using one or more imaging devices on the access port 170. In one embodiment, the display 186 may be removably mountable on the hub 182, which may include one or more connectors or cables (not shown) that may be coupled to corresponding connectors on the hub 182. Alternatively, the display 186 may be permanently mounted to the hub 182. In a further alternative, a display may be provided separate from the access port 170 and images may be transmitted wirelessly or via wired connection from the access port 170, similar to other embodiments herein.

Each sleeve 184 may include an elongate tubular body, e.g., formed from stainless steel or other metal, plastic, and/or composite material including a lumen for carrying one or more imaging components. The sleeves 184 may be substantially rigid or, alternatively, may be sufficiently flexible to follow the shape of the lumens 178b, e.g., if the tubular body 172 is malleable or flexible and directed to a nonlinear shape.

In an exemplary embodiment, at least one of the imaging sleeves 184 may carry a CMOS, CCD, or other camera (not shown) on its distal tip 184b to acquire the images. Alternatively, a lens may be provided on the distal tip 184b and a fiberoptic cable or other optical conductor (also not shown) may extend through the imaging sleeve 184 to the proximal end 184a, where the conductor may be coupled to a camera to acquire the images.

Figure 13B:
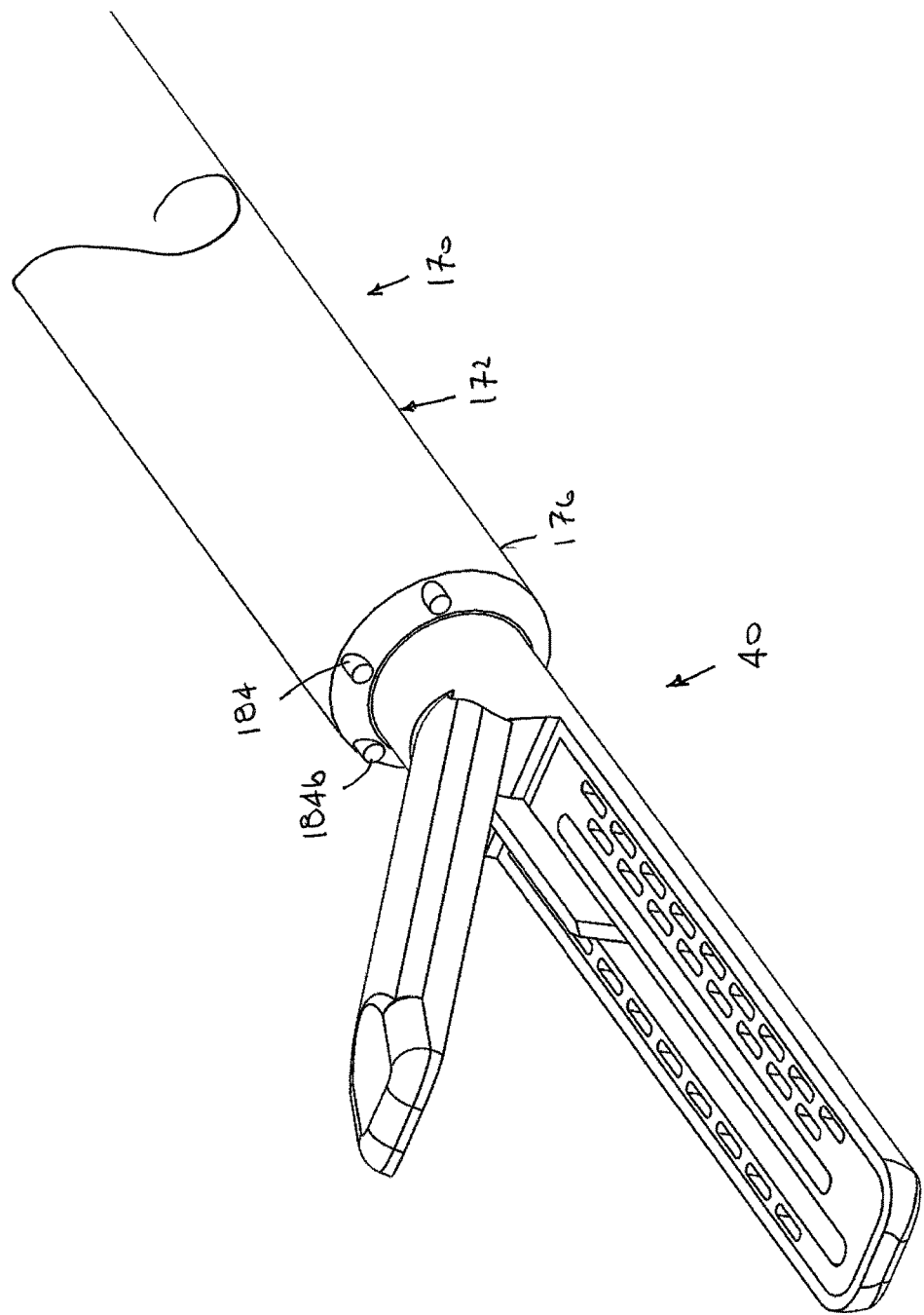
FIG. 13B is a detail of a distal end of the access port of FIG. 13A showing an end effector of the stapler apparatus.

Similarly, at least one of the imaging sleeves 184 may carry an illumination source, e.g., an LED or other light source, on its distal tip 184b for transmitting light beyond the distal end 176 of the tubular body 172. Alternatively, the LED or other light source may be provided within the hub 180, and an optical conductor may extend from the proximal end 184a of the imaging sleeve 184 to its display tip 184b. In the example shown, the video module 180 includes a pair of sleeves 184 on opposite sides of the primary lumen 178a carrying cameras on distal tips 184(1), and a pair of sleeves 184 on opposite sides of one of the camera sleeves carrying an LED or other illumination source on the distal tips 184(2) (or may carry lenses coupled to cameras or LEDs), e.g., providing a field of view as shown in FIG. 9C. In this configuration, images may be acquired substantially simultaneously from opposite distal tips 184b(1) to provide binocular imaging on either side of the end effector 40 (as shown in FIG. 13B), with the distal tips 184b(2) providing off-axis illumination to minimize shadows or otherwise enhance illumination within a surgical space.

During use, the imaging elements 184 may be inserted into inlets 175b from the proximal end 174 of the tubular body 172 into the corresponding secondary lumens 178b until the distal tips 184b are positioned adjacent the distal end 176 of the tubular body 172, e.g., extending a desired distance from the outlets 179b to allow acquisition of images. Optionally, when the imaging elements 184 are fully inserted, connectors on the hub 182 and/or proximal end 174 may engage to secure the video module 180 relative to the tubular body 172. The assembled access port 170 may then be introduced into a patient's body to allow introduction of one or more instruments to be introduced to perform a surgical procedure while acquiring images of the procedure, similar to other embodiments herein. For example, as shown in FIGS. 13A and 13B, an end effector 40 of a stapler apparatus 8 may be inserted through the primary lumen 178a to staple and/or remove tissue, as described elsewhere herein.

Upon completing the procedure, any instruments may be removed from the primary lumen 178a, and the port 170 may be removed from the patient's body using conventional methods. The video module 180 may be removed from the tubular body 172 and then cleaned, sterilized, and/or otherwise prepared for use again in a subsequent procedure. The tubular body 172 may be single-use, and may be discarded after the procedure. Alternatively, the tubular body 172 may also be cleaned, sterilized, and/or otherwise prepared for reuse.

Figure 14:
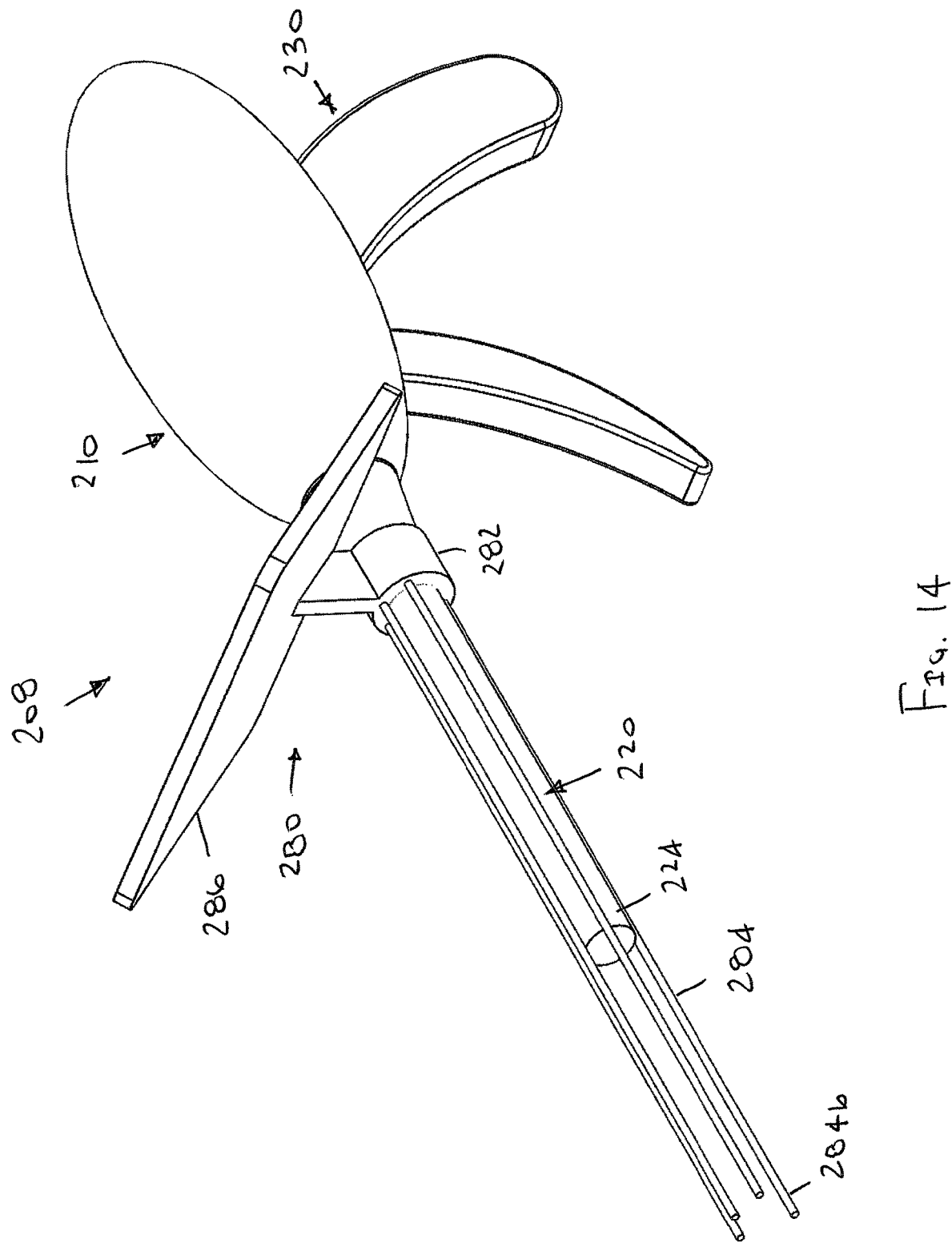
FIG. 14 is a perspective view of another embodiment of a stapler apparatus including an integral video module including a display and a plurality of imaging sleeves extending from a handle of the apparatus and insertable into an end effector (not shown).

Turning to FIG. 14, another exemplary embodiment of a stapler apparatus 208 is shown that includes a video module 280 integrated into a reusable shaft/handle portion 210. Generally, the handle portion 210 includes a shaft 220 extending from a handle 230 including actuation components (not shown), e.g., such that a disposable end effector (not shown) may be coupled to a distal end 224 of the shaft 220, similar to other embodiments herein.

Unlike the previous embodiments, a plurality of elongate imaging sleeves 284 also extend from the handle portion 210, e.g., from a hub 282 from which the shaft 220 also extends. As shown, the imaging sleeves 284 may be positioned radially around the shaft 220 and may have a length longer than the shaft 220 such that distal tips 284b of the imaging sleeves 284 extend distally beyond the distal end 224 of the shaft 220. The video module 280 may also include a display 286 mounted on the hub 282 (or elsewhere on the handle portion 210 and/or remote from the apparatus 280, as desired) coupled to one or more cameras and/or illumination sources (not shown) that may be used to acquire images beyond the distal tips 184b.

An end effector (not shown) may be coupled to the distal end 224 of the shaft 220 generally similar to other embodiments, e.g., to staple, cauterize, and/or remove tissue. In addition, the housing of the end effector may include a plurality of secondary lumens (also not shown) that may receive the imaging sleeves 284 such that the distal tips 284b are disposed adjacent jaws of the end effector, e.g., similar to the configuration shown in FIG. 13B.

During use, a desired end effector may be received over the imaging sleeves 284 and coupled to the distal end 224 of the shaft. Optionally, a cartridge (not shown) may be loaded into one of the jaws of the end effector and then the end effector may be introduced into a patient's body to perform a surgical or other medical procedure, similar to other embodiments herein. IN this manner, the video module 280 may be used to acquire images during the procedure. Upon completing the procedure, the apparatus 208 may be removed, the end effector may be removed and, optionally discarded, and the handle portion 210 may be cleaned and/or otherwise prepared for use in another procedure, also similar to other embodiments herein.

Alternatively, it will be appreciated that other staples or clips may be delivered using any of the stapler apparatus herein, such as those described in the provisional application incorporated by reference herein.

It will be appreciated that elements or components shown with any embodiment herein are exemplary for the specific embodiment and may be used on or in combination with other embodiments disclosed herein. In addition, although the apparatus herein have been described for particular use during an appendectomy procedure. It will be appreciated that the apparatus and methods herein may be used in a variety of surgical procedures, e.g., including open, minimally invasive, laparoscopic, and other procedures, where it is desired to staple and remove target tissues, e.g., within a patient's intestine, lungs, vasculature, and other locations.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A staple for delivery into tissue, comprising:
a base element including first and second ends;
a first tine extending from the first end substantially perpendicular to the base, the first tine having a first length from the base to a first tip of the first tine and including a plurality of notches located on an inside surface of the first tine and spaced apart from one another along the first length between the base and the first tip, each of the notches including a blunt upper edge and a tapered lower edge; and
a second tine extending from the second end substantially perpendicular to the base to a second tip, the second tine having a second length longer than the first length such that, when the second tine is bent adjacent the base towards the first tine, the notches provide a ratchet allowing the second end to travel downwardly into the notches sequentially but preventing the second tip from moving upwardly out of the notches.

2. The staple of claim 1, wherein the base includes a base length between the first and second tines, and wherein the second length is longer than the base length such that the second tip is receivable in the one or more botches.

3. The staple of claim 1, wherein the base, first tine, and second tine have a substantially uniform cross-section.

4. The staple of claim 3, wherein the cross-section is one of rectangular, oblong, or flattened circular.

5. The staple of claim 3, wherein the base, first tine, and second tine lie within a plane, and wherein the cross-section of the staple defines a major dimension perpendicular to the plane and a minor dimension within the plane, the major dimension larger than the minor dimension.

6. The staple of claim 1, wherein the base defines an axis extending between the first and second ends, and wherein the base includes a non-linear shape between the first and second ends that extends transversely relative to the axis.

7. The staple of claim 6, wherein the non-linear element comprises a bump that extends laterally from the axis.

8. The staple of claim 1, further comprising rounded transitions at the first and second ends transitioning from the base to the first and second tines.

9. The staple of claim 8, wherein the rounded transition from the base to the second tine has a larger radius of curvature than the rounded transition from the base to the first tine.

10. A staple for delivery into tissue, consisting of:
a substantially straight base element including first and second ends;
a first substantially straight tine extending from the first end substantially perpendicular to the base, the first tine having a first length from the base to a first tip of the first tine and including a plurality of notches located on an inside surface of the first tine and spaced apart from one another along the first length, each of the notches including a blunt upper edge and a tapered lower edge; and
a second tine substantially straight extending from the second end substantially perpendicular to the base to a second tip, the second tine having a second length longer than the first length and configured such that, when the second tine is bent adjacent the base towards the first tine, the notches provide a ratchet allowing the second end to travel downwardly into the notches sequentially but preventing the second tip from moving upwardly out of the notches.

11. The staple of claim 10, wherein the base includes a base length between the first and second tines, and wherein the second length is longer than the base length such that the second tip is receivable sequentially in the notches.

12. A staple for delivery into tissue, comprising:
a substantially straight base element including first and second ends;
a first substantially straight tine extending from the first end substantially perpendicular to the base, the first tine having a first length from the first end to a first tip of the first tine; and
a second substantially straight tine extending from the second end substantially perpendicular to the base to a second tip, the second tine having a second length from the second end to a second tip of the second tine that is longer than the first length and longer than the length of the straight base such that, when the second tine is bent adjacent the base, the second tip of the second tine is engaged in the one or more notches located on the first tine,
wherein the first tine includes a plurality of notches spaced apart from one another along an inner surface of the first length between the first end and the first tip to provide a ratchet allowing the second end to travel downwardly into the notches sequentially.

13. The staple of claim 12, wherein each of the notches is located on an inside surface of the first tine and includes a blunt upper edge such that, when the second tip of the second tine is received in each notch, respectively, the second tip cannot move upwardly out of the notch.

14. The staple of claim 12, wherein each of the notches including a blunt upper edge and a tapered lowed edge to provide a ratchet allowing the second end to travel downwardly into the notches sequentially but prevent the second tip from moving upwardly out of the notches.

15. The staple of claim 1, wherein a transition between the second tine and the base is configured to reduce the force to bend the second tine towards the first tine.

16. The staple of claim 1, wherein the base comprises a bump between the first and second tines configured to pinch tissues entrapped within the staple.

17. The staple of claim 1, wherein the base is substantially straight between the first and second ends.

* * * * *